US010004669B2

(12) United States Patent
Eckert et al.

(10) Patent No.: US 10,004,669 B2
(45) Date of Patent: Jun. 26, 2018

(54) DENTAL COMPOSITION AND USE THEREOF

(71) Applicant: 3M INNOVATIVE PROPERTIES COMPANY, St. Paul, MN (US)

(72) Inventors: Adrian S. Eckert, Herrsching (DE); Michael Cub, Munich (DE); Bettina Hailand-Newhook, Ammersee (DE); Marion B. Kestel, Munich (DE); Christoph Thalacker, Wilheim (DE); Karsten Dede, Landsberg (DE); Uwe H. Hoheisel, Tuerkenfeld (DE); Reinhold Hecht, Kaufering (DE); Henry Loll, Gilching (DE); Bernhard Hofmann, Peissenberg (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days. days.

(21) Appl. No.: 15/119,241

(22) PCT Filed: Feb. 18, 2015

(86) PCT No.: PCT/US2015/016246
§ 371 (c)(1),
(2) Date: Aug. 16, 2016

(87) PCT Pub. No.: WO2015/126862
PCT Pub. Date: Aug. 27, 2015

(65) Prior Publication Data
US 2017/0056298 A1    Mar. 2, 2017

(30) Foreign Application Priority Data

Feb. 18, 2014  (EP) ..................... 14155580

(51) Int. Cl.
*A61K 6/083* (2006.01)
*A61K 6/00* (2006.01)
*C08L 33/00* (2006.01)

(52) U.S. Cl.
CPC .............. *A61K 6/083* (2013.01); *A61K 6/005* (2013.01); *A61K 6/0052* (2013.01); *A61K 6/0073* (2013.01); *A61K 6/0088* (2013.01); *A61K 6/0091* (2013.01)

(58) Field of Classification Search
USPC ........ 523/116; 433/217.1, 222.1, 223, 228.1; 106/35
See application file for complete search history.

(56) References Cited

U.S. PATENT DOCUMENTS

| 3,541,068 A | 11/1970 | Taylor |
| 3,729,313 A | 4/1973 | Smith |
| 3,741,769 A | 6/1973 | Smith |
| 3,808,006 A | 4/1974 | Smith |
| 3,853,962 A | 12/1974 | Gander |
| 4,071,424 A | 1/1978 | Dart |
| 4,250,053 A | 2/1981 | Smith |
| 4,259,075 A | 3/1981 | Yamauchi |
| 4,394,403 A | 7/1983 | Smith |
| 4,499,251 A | 2/1985 | Omura |
| 4,537,940 A | 8/1985 | Omura |
| 4,539,382 A | 9/1985 | Omura |
| 4,544,742 A | 10/1985 | Schmitt |
| 4,642,126 A | 2/1987 | Zador |
| 4,652,274 A | 3/1987 | Boettcher |
| 4,737,593 A | 4/1988 | Ellrich |
| 4,744,827 A | 5/1988 | Winkel |
| 4,772,530 A | 9/1988 | Gottschalk |
| 4,872,936 A | 10/1989 | Engelbrecht |
| 4,874,450 A | 10/1989 | Gottschalk |
| 4,954,414 A | 9/1990 | Adair |
| 5,055,372 A | 10/1991 | Shanklin |
| 5,057,393 A | 10/1991 | Shanklin |
| 5,130,347 A | 7/1992 | Mitra |
| 5,530,038 A | 6/1996 | Yamamoto |
| 5,545,676 A | 8/1996 | Palazzotto |
| 5,624,260 A | 4/1997 | Wilcox |
| 5,865,803 A | 2/1999 | Major |
| 5,893,714 A | 4/1999 | Arnold |
| 5,918,772 A | 7/1999 | Keller |
| 5,944,419 A | 8/1999 | Streiff |
| 6,444,725 B1 | 9/2002 | Trom |
| 6,458,868 B1 | 10/2002 | Okada |
| 6,730,156 B1 | 5/2004 | Windisch |
| 6,769,912 B2 | 8/2004 | Beuschel |
| 6,899,948 B2 | 5/2005 | Zhang |
| 8,329,776 B2 | 12/2012 | Hecht |

(Continued)

FOREIGN PATENT DOCUMENTS

| DE | 1495520 | 4/1969 |
| DE | 1921869 | 7/1970 |

(Continued)

OTHER PUBLICATIONS

Antonucci, "Dimethacrylates Derived from Hydroxybenzoic Acids", Journal of Dental Research, 1976, vol. 55, No. 1, pp. 8-15.

(Continued)

*Primary Examiner* — Tae H Yoon

(57) ABSTRACT

The invention relates to a dental composition comprising polymerizable monomer (1), initiator component(s), filler component(s) in an amount of more than about 20 wt.-%, wt.-% with respect to the whole weight of the composition, the polymerizable monomer (1) being characterized as follows: having exactly two (meth)acrylate reactive moieties, having an unsymmetrical backbone as linkage between the (meth)acrylate reactive moieties, the two (meth)acrylate reactive moieties being attached onto the unsymmetrical monomer backbone as alkyl esters, the unsymmetrical backbone comprising one aromatic moiety of the phenolic type, the polymerizable monomer (1) not containing an acidic moiety, other atoms than carbon, hydrogen, and oxygen, bisphenol moieties. The invention also relates to the use of the dental composition as or for producing a dental filling material, crown and bridge material, inlay, onlay, veneer or dental mill blank.

16 Claims, No Drawings

(56) References Cited

U.S. PATENT DOCUMENTS

| | | |
|---|---|---|
| 2003/0008967 A1 | 1/2003 | Hecht |
| 2003/0132539 A1 | 7/2003 | Althoff |
| 2005/0236586 A1 | 10/2005 | Hartung |
| 2006/0187752 A1 | 8/2006 | Keller |
| 2007/0090079 A1 | 4/2007 | Keller |
| 2007/0172789 A1 | 7/2007 | Muller |
| 2010/0069469 A1* | 3/2010 | Young .................... A61K 6/033 514/44 R |
| 2010/0076115 A1 | 3/2010 | Utterodt |
| 2011/0315928 A1 | 12/2011 | Jin |
| 2012/0068388 A1 | 3/2012 | Sakamoto |

FOREIGN PATENT DOCUMENTS

| | | |
|---|---|---|
| EP | 0059451 | 9/1982 |
| EP | 0115709 | 8/1984 |
| EP | 0455854 | 11/1991 |
| EP | 0712622 | 5/1996 |
| EP | 1051961 | 11/2000 |
| EP | 1340472 | 9/2003 |
| JP | 61-012709 | 1/1986 |
| WO | WO 2009-006282 | 1/2009 |
| WO | WO 2009-042574 | 4/2009 |
| WO | WO 2009-151957 | 12/2009 |
| WO | WO 2012-003136 | 1/2012 |
| WO | WO 2012-106083 | 8/2012 |

OTHER PUBLICATIONS

International Search Report for PCT International Application No. PCT/US2015/016246, dated May 29, 2015, 4 pages.

\* cited by examiner

DENTAL COMPOSITION AND USE THEREOF

CROSS-REFERENCE TO RELATED APPLICATIONS

This application is the § 371 U.S. National Stage of International Application No. PCT/US2015/016246, filed 18 Feb. 2015, which claims the benefit of EP Provisional Application No. 14155580.5, filed 18 Feb. 2014, the disclosures of which are incorporated by reference herein in their entireties.

FIELD OF THE INVENTION

The invention relates to a dental composition which is in particular useful for restorative purposes. The composition comprises a hardenable resin matrix comprising non-acidic hardenable components, a filler and an initiator and shows improved physical properties like compressive strength.

BACKGROUND ART

There are different dental filling materials which are used for restorative purposes, including amalgam and dental composite materials.

In order to fulfill its function (replacement of lost tooth structure), dental filling materials need to have adequate physical properties. In particular, they have to have sufficient strength to be able to absorb and resist chewing forces.

If, however, the material is too hard, it will also become more brittle.

Thus, a dental filling material not only needs to be sufficiently hard, but also needs to be to some extend flexible.

To address these needs, commercially available dental composite filling materials typically contain a certain amounts of resin matrix, filler and initiator.

A widely used polymerizable (meth)acrylate component contained in the resin matrix is bisphenol A-glycidyl methacrylate (Bis-GMA) or other bisphenol based (meth)acrylate monomers.

Compositions containing bisphenol-based monomers are said to have a variety of advantageous properties like high compressive strength, thus enabling the practitioner to formulate a variety of different dental compositions for restorative purposes.

Some literature, however, seems to indicate that bisphenol based monomers are not always recommended for all purposes. Alternative polymerizable (meth)acrylate components are thus needed.

US 2010/076115 (Heraeus Kulzer) relates to compositions for dental composites comprising acrylic acid esters of tricyclo[5.2.1.02.6] decane with urethane groups U.S. Pat. No. 3,853,962 (Gander) relates to dental restorative cements comprising the methacrylate monomer 1,3-bis [2-,3-di(methacryloxy)-propoxy]-benzene. Restorative compositions containing this kind of monomer are said to have improved compressive strength and related physical properties.

U.S. Pat. No. 4,744,827 (Winkel) describes (meth)acrylic acid derivatives of a tricyclodecane exhibiting considerably less polymerization shrinkage.

WO 2012/003136 (3M) relates to a dental composition comprising a hardenable compound with a comparable rigid backbone, which may comprise urethane moieties. The composition is said to have advantageous properties e.g. with respect to shrinkage stress.

WO 2009/042574 (3M) describers methacrylate based monomers containing a urethane linkage showing a well balanced properties with respect to viscosity, refractive index, molecular weight and shrinkage value.

U.S. Pat. No. 4,539,382 (Omura et al) describes a method of restoring a carious tooth, the method comprising applying to the wall surface of a cavity in a carious tooth an adhesive composition comprising a certain amount of a certain polymerizable monomer, a certain amount of a copolymerizable vinyl monomer and a certain amount of a curing agent, and filling said cavity with a dental filling composition.

US 2011/0315928 A1 (Jin at al.) relates to a low viscosity and low stress dental composition comprising at least one low stress polymerizable resin and at least one filler. The dental composition are said to have high depth of cure and self-leveling characteristics and are capable of bulk application.

WO 2012/106083 A1 (3M) relates to a dental composition comprising a certain compound (A), a filler (B), and an initiator (C), wherein compound (A) comprises a certain backbone unit and one or two spacer units having a certain structure.

JP 61-012709 (Mitsui) relates to a composition containing poly(methacryloxypolyethoxy)benzene, vinyl compounds and a curing catalyst, giving cured products of high water resistance and being suitable for dental purposes.

J. M. Antonucci et al. describes in J. Dent. Res. 1976, 55:8 the synthesis of dimethacrylates derived from hydroxybenzoic acids. The obtained monomers are said to be crystalline and are suggested for possible evaluation in composites and pit and fissure sealant formulations, however, without describing any working example.

DESCRIPTION OF THE INVENTION

Generally, there is a need for a dental composition having adequate physical properties, which can be formulated without the need of using Bis-GMA or other bisphenol based (meth)acrylate monomers or components.

In particular, it is one object of the present invention to provide a dental composition showing improved physical properties, like compressive strength, wherein the dental composition ideally does not comprise bisphenol moieties containing (meth)acrylate components.

To address this object, the present invention features a dental composition as described in the claims comprising
  Polymerizable monomer (1),
  Initiator component(s),
  Filler component(s) in an amount of more than about 20 wt.-%, wt.-% with respect to the whole weight of the composition,
the polymerizable monomer (1) being characterized as follows:
  having exactly two (meth)acrylate reactive moieties,
  having an unsymmetrical backbone as linkage between the (meth)acrylate reactive moieties,
  the two (meth)acrylate reactive moieties being attached onto the unsymmetrical monomer backbone as alkyl esters,
  the unsymmetrical backbone comprising typically exactly one aromatic moiety of the phenolic type,
the polymerizable monomer (1) not containing
  other atoms than carbon, hydrogen, and oxygen,
  other aromatic moieties than aromatic moieties of the phenolic type,
  bisphenol moieties.

Moreover, the invention features a method of using the composition as described in the text of the invention for producing or as dental filling material, crown and bridge material (e.g. temporary and long-term), inlay, onlay, veneer, orthodontic device or dental mill blank.

The invention is also related to the use of the dental composition as described in the present text for producing a dental restoration like a dental crown, bridge, onlay or inlay by applying a rapid-prototyping technique.

Unless defined differently, for this description the following terms shall have the given meaning:

A "dental composition" or a "composition for dental use" or a "composition to be used in the dental field" is any composition which can and is to be used in the dental field. In this respect the composition should not be detrimental to the patients' health and thus free of hazardous and toxic components being able to migrate out of the composition. Examples of dental compositions include permanent and temporary crown and bridge materials, artificial crowns, anterior or posterior filling materials, dental mill blanks and orthodontic devices.

Dental compositions are typically hardenable compositions. Dental compositions for hardening in the mouth can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is typically within these ranges.

A "dental filling material" is a hardenable material designed to restore missing tooth structure, in particular to fill a cavity in hard dental tissue.

A "crown and bridge material" within the meaning of the invention is a hardenable material used for making dental crowns and bridges. These materials are typically used during the time period a dental technician needs for producing a permanent prosthetic work such as a crown or bridge. These time periods can last from a few days (1 to about 6 days), a few weeks (1 to about 4 weeks) or a few months (1 to about 6 month). A long term crown and bridge material is typically used over a time period of about 6 to 24 months.

By "dental milling block" or "dental mill blank" is meant a solid block (3-dim article) of material from which a dental article can be machined. A dental milling block has typically a geometrically defined shape. A dental milling block may have a size of about 20 mm to about 30 mm in two dimensions, for example may have a diameter in that range, and may be of a certain length in a third dimension. A block or blank for making a single crown may have a length of about 15 mm to about 30 mm, and a block or blank for making bridges may have a length of about 40 mm to about 80 mm. A typical size of a block or blank as it is used for making a single crown has a diameter of about 24 mm and a length of about 19 mm. Further, a typical size of a block or blank as it is used for making bridges has a diameter of about 24 mm and a length of about 58 mm. Besides the above mentioned dimensions, a dental milling block may also have the shape of a cube, a cylinder or a cuboid. Larger milling blocks may be advantageous if more than one crown or bridge should be manufactured out of one blank. For these cases, the diameter or length of a cylindric or cuboid shaped mill blank may be in a range of about 80 to about 200 mm, with a thickness being in the range of about 10 to about 30 mm.

By "machining" is meant milling, grinding, cutting, carving, or shaping a material by a machine. Milling is usually faster and more cost effective than grinding.

An "initiator system" or "initiator" shall include those components of the dental composition being able to start or initiate the curing process of the hardenable components, also described herein as "curing the hardenable components".

A "resin matrix" shall mean the organic part of the dental composition being composed of the hardenable components and organic diluents, if present.

A "hardenable component or material" (e.g., "polymerizable component" or "crosslinkable component") is any component which can be cured or solidified e.g., by heating to cause polymerization, chemical crosslinking, radiation-induced polymerization or crosslinking by using a redox initiator. A hardenable component may contain, for example, only one, two, three or more polymerizable groups. Typical examples of polymerizable groups include unsaturated carbon groups, such as a vinyl group being present e.g. in a (meth)acrylate group.

A "curable composition" is a mixture of two or more components, the mixture being able to be cured or solidified e.g., by heating to cause chemical crosslinking, radiation-induced polymerization or crosslinking by using a redox initiator. A curable composition may advantageously include a hardenable component.

A "monomer" is any chemical substance which can be characterized by a chemical formula, bearing one or more polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth)acryloxy" group is a shorthand term referring to either an acryloxy group (i.e., $CH_2=CH-C(O)-O-$) and/or a methacryloxy group (i.e., $CH_2=C(CH_3)-C(O)-O-$). Similarly, (meth)acrylate is a shorthand term referring to "acrylate" and/or "methacrylate."

"Curing," "hardening," and "setting reaction" are used interchangeably and refer to a reaction wherein physical properties such as viscosity and hardness of a composition change (e.g., increase) over time due to a chemical reaction between the individual components.

A "polymerizable monomer(s) with acidic moieties" is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, phosphonic acid residues such as C—P(O)(OH)OH, sulfonic acid residues, such as —SO$_3$H or sulfinic acid residues such as —SO$_2$H.

A "phenolic type" moiety is generally understood as an aromatic moiety bearing at least one oxygen atom directly attached onto an aromatic residue, more precisely, a moiety comprising the structural element [C6RxO] with x being 1, 2, 3, 4, 5 or 6, R being H, alkyl (e.g. C1 to C8), —O—, —CO— or —C(O)O— and C6 forming an aromatic ring.

For example, "C6H5O—" (phenoxy) represents the most simple "phenolic type" moiety.

A "powder" means a dry, bulk solid composed of a large number of very fine particles that may, for example, flow freely when shaken or tilted.

A "particle" means a substance being a solid having a shape which can be geometrically determined. Particles can typically be analysed with respect to e.g. particle size or diameter. Particles may be amorphous or crystalline.

"Radiation curable" shall mean that the component (or composition, as the case may be) can be cured by applying radiation, preferably electromagnetic radiation with a wavelength in the visible light spectrum under ambient conditions and within a reasonable time frame (e.g. within about 15, 10 or 5 min).

The term "visible light" is used to refer to light having a wavelength of about 400 to about 700 nanometers (nm).

"Hard dental tissue" means dentin and enamel.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions can be adjusted to about 23° C. and about 1013 mbar and about 50% relative humidity. In the dental and orthodontic field ambient conditions are reasonably understood as a pressure of about 950 to about 1050 mbar, temperature of about 15 to about 40° C. and relative humidity of about 20 to about 80%.

A composition is "essentially or substantially free of" a certain component within the meaning of the invention, if the composition does not contain said component as an essential feature. Thus, said component is not willfully added to the composition either as such or in combination with other components or ingredient of other components. A composition being essentially free of a certain component usually contains the component in an amount of less than about 1 wt.-% or less than about 0.1 wt.-% or less than about 0.01 wt.-% with respect to the whole composition. Ideally, the composition or solution does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about."

DETAILED DESCRIPTION OF THE INVENTION

It has been found that the composition described in the present text is superior with respect to a variety of properties:

A hardened dental composition comprising the asymmetric (i.e. non symmetric), polymerizable monomers described in the present text shows improved physical properties, especially with respect to compressive strength.

Further, the desired dental composition can be formulated without using bisphenol moiety(s) containing monomers or components.

The asymmetric, polymerizable monomers described in the present text typically do not solidify at room temperature and thus facilitate the incorporation of a sufficient amount of filler, an amount which is typically needed for formulating or producing a dental filling or crown and bridge material or dental mill blank.

In certain embodiments the dental composition fulfills at least one or more, sometimes all of the following features before hardening:
  Viscosity: being a paste, e.g. having a viscosity from about 0.5 to about 200 Pa*s or from about 1 to about 100 Pa*s measured at 23° C. with a shear rate of 100 l/s;
  pH value, if brought in contact with water: neutral (e.g. about 6 to about 8) or acidic (e.g. about 2 to about 5);
  radiation or redox curable;
  storage stable;
  being provided as a one or two-component system.

If desired and more precisely, the viscosity can be determined under the following conditions: 23° C.; shear rate: 100 l/s; measured with a cone/plate geometry CP25-1 with a Physica MCR 301 Rheometer, Anton Paar GmbH, Graz, Austria.

If dissolved or dispersed in water (e.g. 1 g composition in 10 ml water) the composition typically exhibits a pH value in the range from about 6 to about 8 or about 7. That is, the composition as a whole essentially has a neutral pH, if brought in contact with water, or is slightly acidic.

The invention provides a composition which can be hardened in an acceptable time frame, e.g., less than about 300 seconds (s) or less than about 180 s or less than about 120 s, and to a sufficient depth using visible light source equipment already available in the dental office.

In certain embodiments the dental composition fulfills at least one or more, sometimes all of the following properties (after hardening):
  compressive strength (CS1) of the dental formulation determined according to ISO 4049 using specimens having the dimension of 3 mm×3 mm×5 mm: at least about 430 MPa or at least about 445 or at least about 460 MPa,
  compressive strength (CS2) of the dental formulation determined according to DIN 53454 (ISO 9917 2001) using cylindrical specimens with a diameter of 4 mm and a height of 8 mm: at least about 280 MPa or at least about 300 or at least about 320 MPa.

The polymerizable monomer (1) is one component of the hardenable resin matrix contained in the dental adhesive composition.

The polymerizable monomer (1) can be described as follows:
  having exactly two (meth)acrylate reactive moieties,
  having an unsymmetrical backbone as linkage between the (meth)acrylate reactive moieties,
  the two (meth)acrylate reactive moieties being attached onto the unsymmetrical monomer backbone as alkyl esters,
  the unsymmetrical backbone comprising exactly one aromatic moiety of the phenolic type, preferably containing not more than one additional aromatic moiety within the unsymmetrical monomer backbone not being part of the linkage between the reactive groups but being attached onto this linkage between the reactive groups, preferably having exactly two (meth)acrylate reactive groups that are always attached onto the unsymmetrical monomer backbone as alkyl esters, the polymerizable monomer (1) not containing
- other atoms than carbon, hydrogen, and oxygen,
- other aromatic moieties than aromatic moieties of the phenolic type,
- bisphenol moieties,
- optionally other oxygen based linkages than ethers and esters.

According to one embodiment, the polymerizable monomer (1) can also be characterized by the following features:
- having a molecular weight of about 300 to about 600,
- not solidifying at room temperature (e.g. 23° C.), that is being a liquid.

Polymerizable monomer (1) is characterized by the following formula (I):

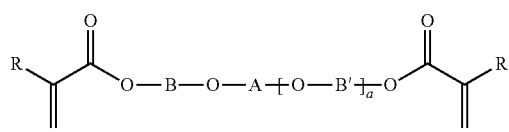

(I)

with:
B—O-A-[—O—B'—]$_a$ representing the unsymmetrical monomer backbone as linkage between the reactive groups,
a=0 or 1,
A being selected from the following moieties:

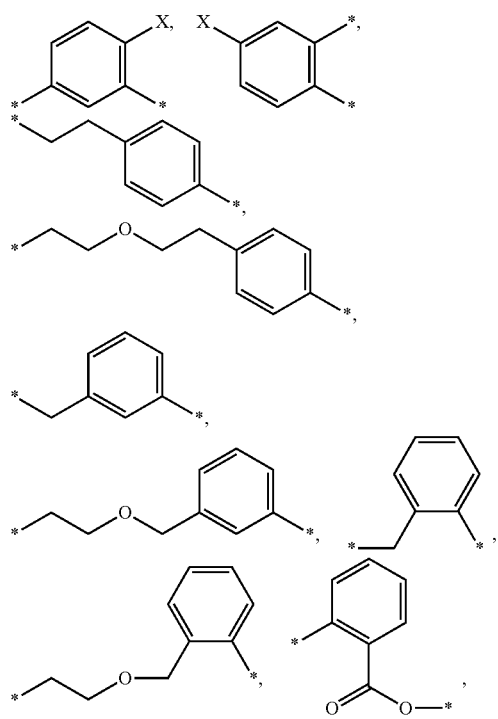

-continued

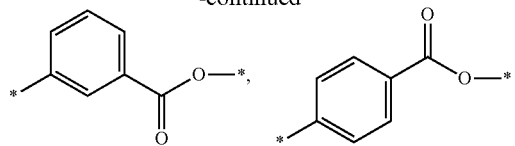

A being always attached as aryl-alkyl ether onto B and/or B',
B being selected from the following moieties:

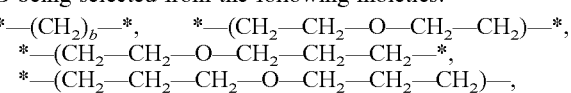

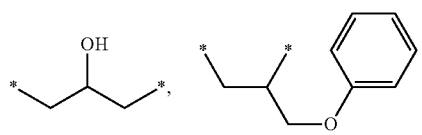

B being always attached as alkyl ester onto the (meth)acrylate reactive moiety,
b=2 to 6,
B' being selected from *—(CH2)$_{b'}$—*, *—(CH$_2$—CH$_2$—O—CH$_2$—CH$_2$)—*,

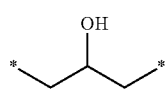

B' being always attached as alkyl ester onto the (meth)acrylate reactive moiety,
b'=2 to 6,
R=H, methyl,
X being selected from H, methyl, ethyl, hexyl, tert-butyl,
"*" representing those sites of a moiety of the monomer, where that moiety is bonded to another moiety of the monomer.

According to a further embodiment the polymerizable monomer (1) can be characterized by either of formula (Ia) or formula (Ib):

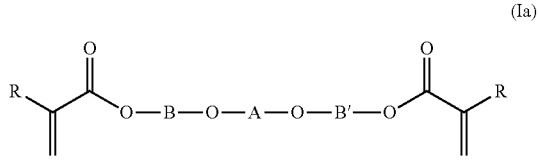

(Ia)

with:
B—O-A-O—B' being an unsymmetrical monomer backbone as linkage between the reactive moieties,
A being selected from the moieties:

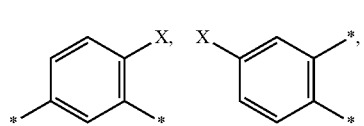

-continued

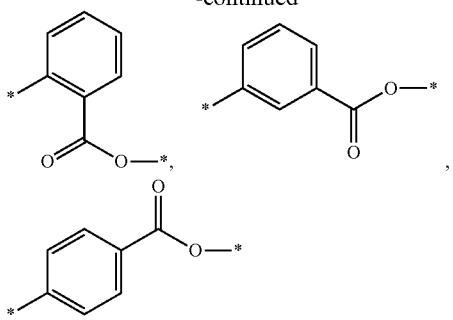

A being always attached as aryl-alkyl ether onto B and B',
B being selected from the moieties:
*—(CH$_2$)$_b$—*,   *—(CH$_2$—CH$_2$—O—CH$_2$—CH$_2$)—*,
*—(CH$_2$—CH$_2$—O—CH$_2$—CH$_2$—CH$_2$)—*,
*—(CH$_2$—CH$_2$—CH$_2$—O—CH$_2$—CH$_2$—CH$_2$)—*,

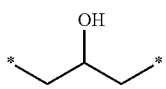

B being always attached as alkyl ester onto the (meth) acrylate reactive moiety,
b=2 to 6,
B' being selected from the moieties:
*—(CH$_2$)$_b$—*,   *—(CH$_2$—CH$_2$—O—CH$_2$—CH$_2$)—*,
*—(CH$_2$—CH$_2$—O—CH$_2$—CH$_2$—CH$_2$)—*,
*—(CH$_2$—CH$_2$—CH$_2$—O—CH$_2$—CH$_2$—CH$_2$)—*

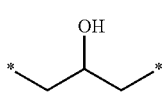

B' being always attached as alkyl ester onto the (meth) acrylate reactive moiety,
b'=2 to 6,
R=H, methyl,
X=H, methyl, ethyl, hexyl, tert-butyl;
or

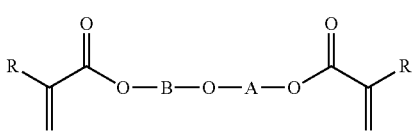 (Ib)

with:
B—O-A being an unsymmetrical monomer backbone as linkage between the reactive moieties,
A being selected from the moieties:

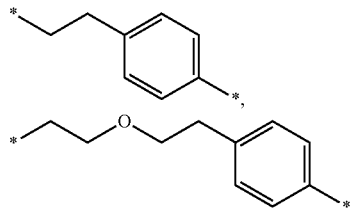

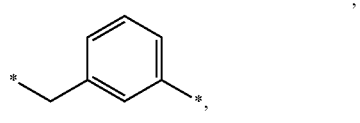

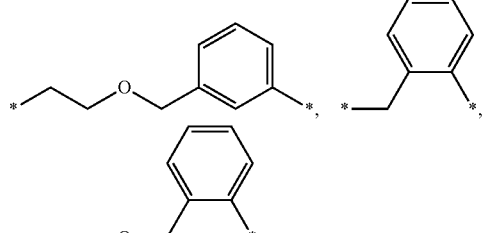

A being always attached as aryl-alkyl ether onto B and always attached as alkyl ester onto the (meth)acrylate reactive moiety,
B being selected from:
—(CH$_2$)$_b$—*, *—(CH$_2$—CH$_2$—O—CH$_2$—CH$_2$)—*,

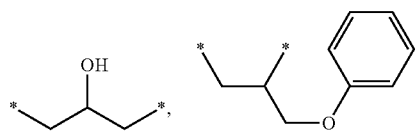

B being always attached as alkyl ester onto the (meth) acrylate reactive moiety,
b=2 to 6,
R=H, methyl;
"*" representing those sites of a moiety of the monomer, where that moiety is bonded to another moiety of the monomer.

Specific examples of for the polymerizable monomer (1) include:

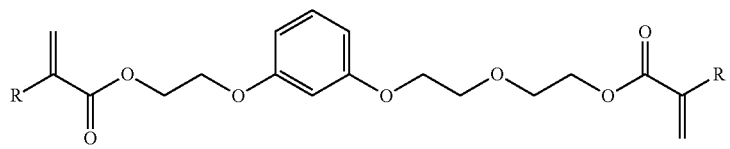

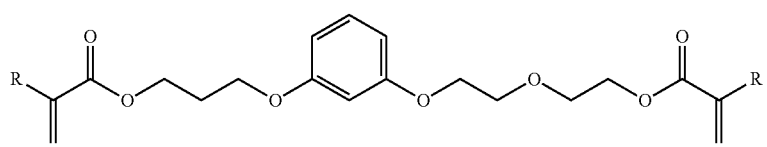

-continued
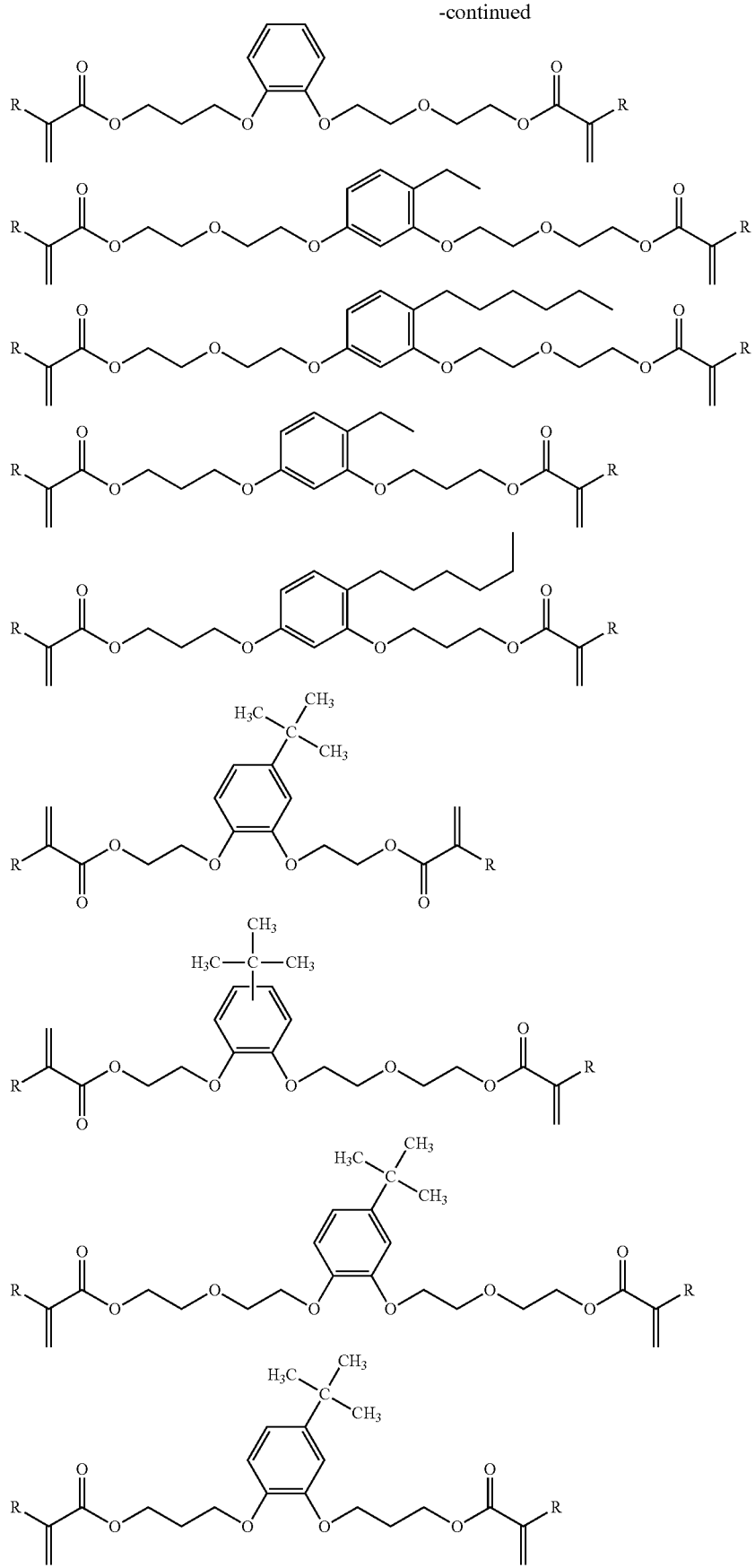

-continued
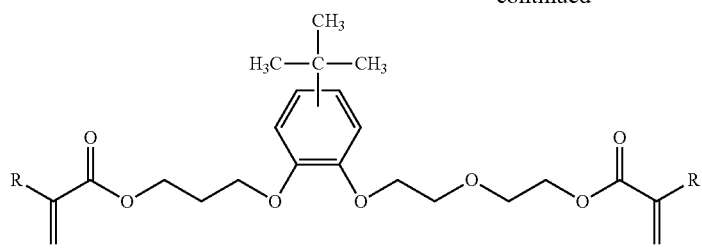
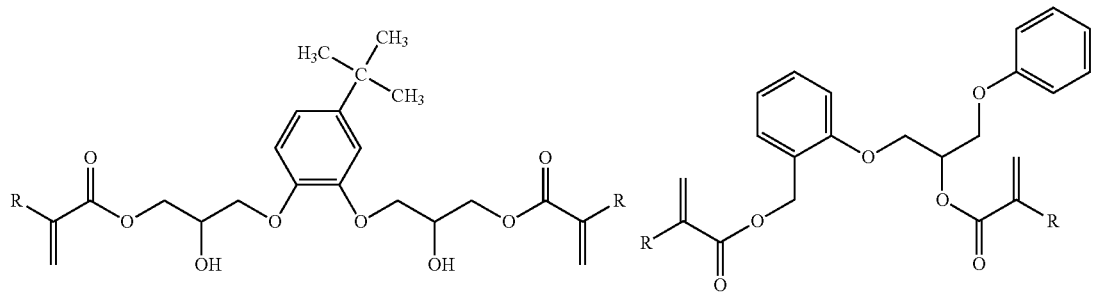
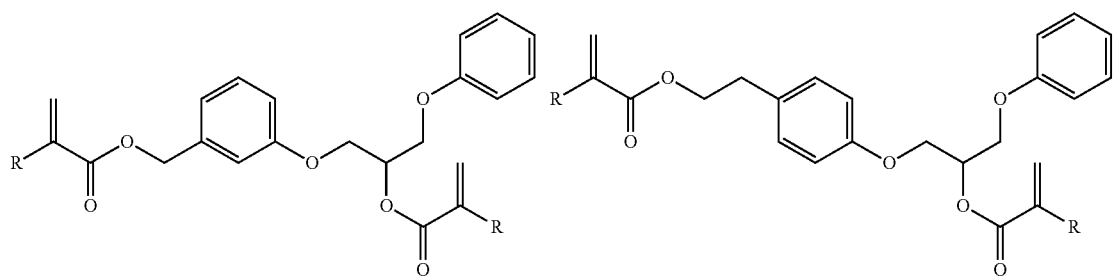
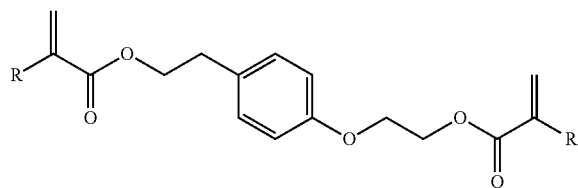
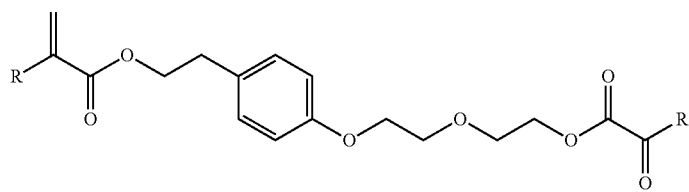
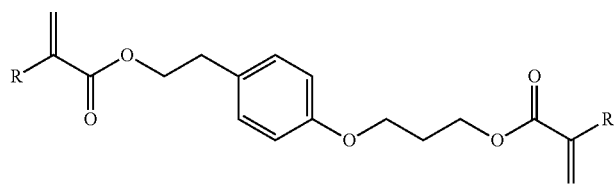
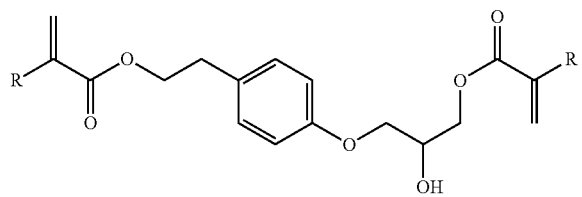

-continued
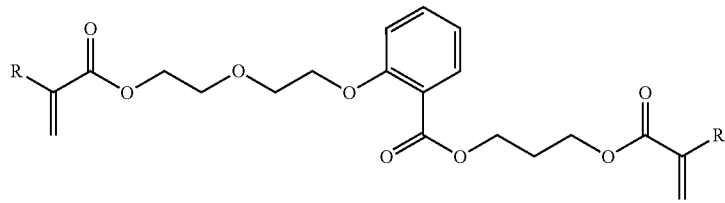
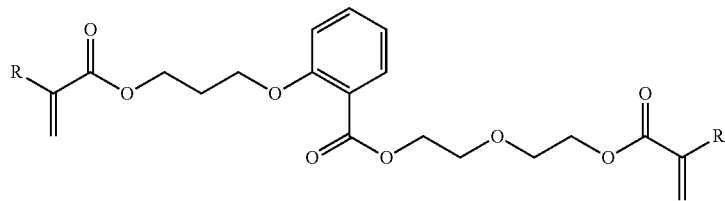
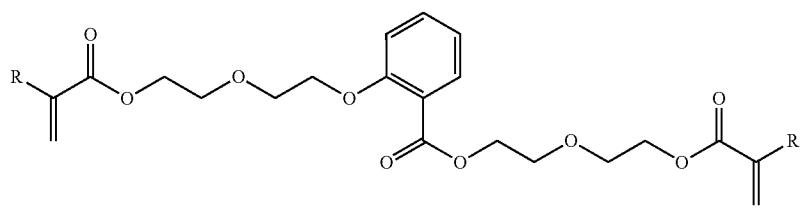
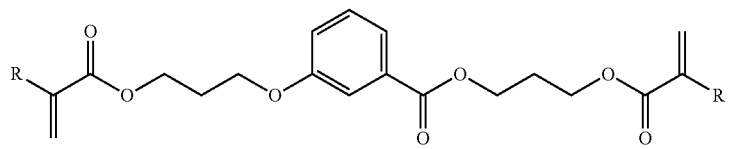
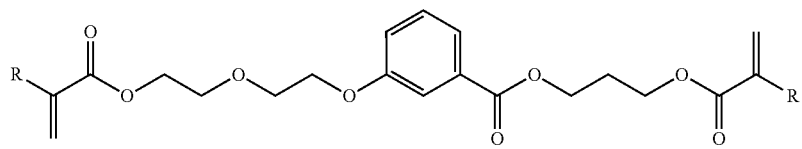
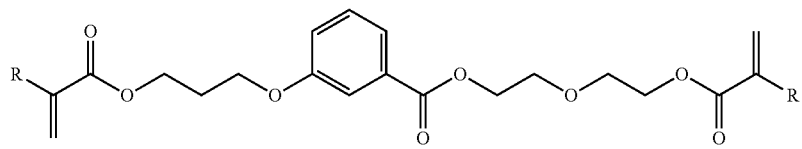
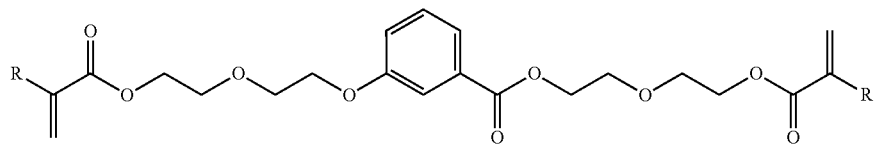
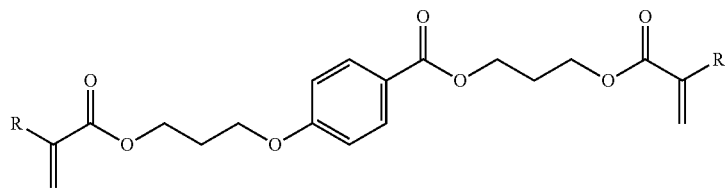

-continued

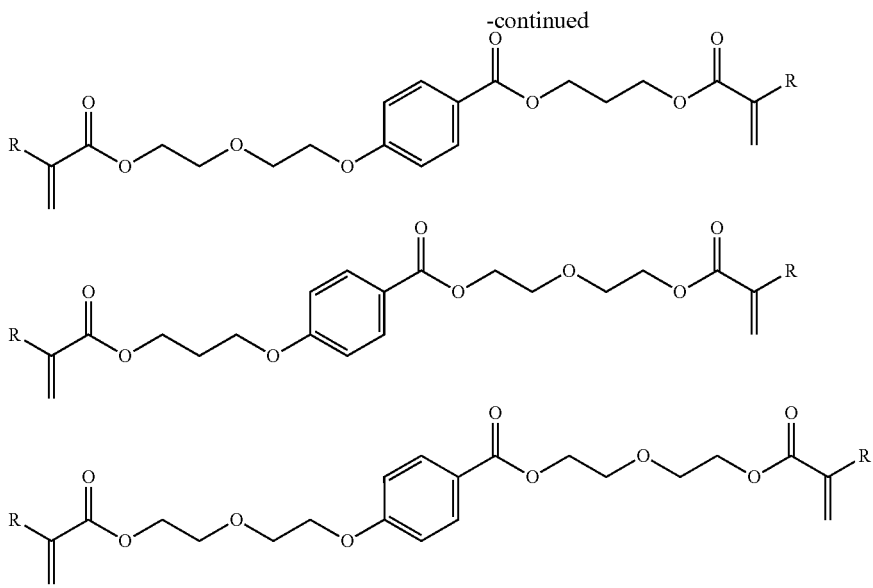

In all the above formulas R can independently be selected from H and CH3, meaning that in each component R can be either methyl or hydrogen, or that one R is methyl and the other R is hydrogen.

The polymerizable monomers (1) described in the present text can be synthesized e.g. as described in the example section below.

When doing so, the skilled person will realize that depending on the polymerizable monomer (1) during synthesis a single non-symmetrical compound is obtained as well as a mixture containing different non-symmetrical components or a mixture containing minor symmetrical components besides the major non-symmetrical compound is obtained.

For a polymerizable monomer (1) containing a non-symmetrical backbone based on a non-symmetrically substituted aromatic moiety, the synthesis will result either in a single non-symmetrical compound or in a composition containing 100 mol-% of non-symmetrical components.

Unless further purified, the synthesis of a polymerizable monomer (1) containing a non-symmetrical backbone which is based on a symmetrically substituted aromatic moiety, will usually result—due to statistics—in a composition containing about 50 mol-% of the non-symmetrical compound as the major component besides about 25 mol-% each of symmetrical compounds as minor components.

Mixtures of two, three or more of the polymerizable monomers (1) can be used, if desired.

The polymerizable monomer (1) is typically contained in the following amounts:
  Lower limit: at least about 1 or at least about 5 or at least about 10 wt.-%
  Upper Limit: up to about 75 or up to about 70 or up to about 65 wt.-%
  Range: from about 1 to about 75 or from about 5 to about 70 or from about 10 to about 65 wt.-%,
wt.-% with respect to the amount of the whole composition.

Besides polymerizable monomer(s) without acidic groups, the composition can also comprise polymerizable monomer(s) with acidic moieties (2) as part of the resin matrix.

Thus, the composition described in the present text may further comprise a polymerizable monomer (2) with an acidic moiety.

If present, the nature and structure of polymerizable monomer (2) is not particularly limited, either unless the desired result cannot be achieved.

The presence of polymerizable monomer (3) can be beneficial because it can provide the composition with a desired acidity.

The polymerizable components with acid moiety (A1) can typically be represented by the following formula $$A_n\text{-}B\text{—}C_m$$

with A being an ethylenically unsaturated group, such as a (meth)acryl moiety,

B being a spacer group, such as (i) linear or branched C1 to C12 alkyl, optionally substituted with other functional groups (e.g. halogenides (including Cl, Br, I), OH or mixtures thereof) (ii) C6 to C12 aryl, optionally substituted with other functional groups (e.g. halogenides, OH or mixtures thereof), (iii) organic group having 4 to 20 carbon atoms bonded to one another by one or more ether, thioether, ester, thioester, thiocarbonyl, amide, urethane, carbonyl and/or sulfonyl linkages, and C being an acidic group, m, n being independently selected from 1, 2, 3, 4, 5 or 6, wherein the acidic group comprises one or more carboxylic acid residues, such as —COOH or —CO—O—CO—, phosphoric acid residues, such as —O—P(O)(OH)OH, phosphonic acid residues, such as C—P(O)(OH)(OH), sulphonic acid residues, such as —SO3H or sulfinic acid residues such as —SO2H.

Examples of polymerizable components with acid moiety include, but are not limited to glycerol phosphate mono (meth)acrylate, glycerol phosphate di(meth)acrylate, hydroxyethyl (meth)acrylate (e.g., HEMA) phosphate, bis((meth)acryloxyethyl) phosphate, (meth)acryloxypropyl phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylate, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like. Derivatives of these hardenable components bearing an acid moiety that can readily react e.g. with water to form the specific examples mentioned above, like acid halides or anhydrides are also contemplated.

Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Using (meth)acrylate functionalized polyalkenoic acids is often preferred as those components were found to be useful to improve properties like adhesion to hard dental tissue, formation of a homogeneous layer, viscosity, or moisture tolerance.

According to one embodiment, the composition contains (meth)acrylate functionalized polyalkenoic acids, for example, AA:ITA:IEM (copolymer of acrylic acid:itaconic acid with pendent methacrylates).

These components can be made by reacting e.g. an AA:ITA copolymer with 2-isocyanatoethyl methacrylate to convert at least a portion of the acid groups of the copolymer to pendent methacrylate groups. Processes for the production of these components are described, e.g., in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Tokuyama Corp.) and EP 1 051 961 A1 (Kuraray Co., Ltd.).

Mixtures of two, three or more of the polymerizable monomers (2) can be used, if desired.

The polymerizable monomer with acidic moieties (2) can be present in the following amounts:
Lower limit: at least about 0 or at least about 0.1 or at least about 1 wt.-%,
Upper Limit: up to about 60 or up to about 50 or up to about 40 wt.-%,
Range: from about 0 to about 60 or from about 0.1 to about 50 or from about 1 to about 40 wt.-%,
wt.-% with respect to the amount of the whole composition.

The composition described in the present text may optionally also comprise a polymerizable monomer (3) without an acidic moiety being different from the polymerizable monomer (1), in particular a polymerizable monomer comprising a urethane moiety.

If present, the polymerizable monomer (3) forms a further component of the hardenable resin matrix.

The nature and structure of polymerizable monomer (3) is not particularly limited, either unless the desired result cannot be achieved.

This component is typically a free-radically polymerizable material, including ethylenically unsaturated monomer, monomers or oligomers or polymers.

Suitable polymerizable components can be characterized by the following formula:

$$A_n\text{-}B\text{-}A_m$$

with A being an ethylenically unsaturated group, such as a (meth)acryl moiety,
B being selected from (i) linear or branched C1 to C12 alkyl, optionally substituted with other functional groups (e.g. halogenides (including Cl, Br, I), OH or mixtures thereof) (ii) C6 to C12 aryl, optionally substituted with other functional groups (e.g. halogenides, OH or mixtures thereof), or (iii) organic group having 4 to 20 carbon atoms bonded to one another by one or more ether, thioether, ester, thioester, thiocarbonyl, amide, urethane, carbonyl and/or sulfonyl linkages,
m, n being independently selected from 0, 1, 2, 3, 4, 5 or 6 with the proviso that n+m is greater 0, that is that at least one A group is present.

Such polymerizable materials include mono-, di- or polyacrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Röhm Plex 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, 1,6 hexandiol di(meth)acrylate, 1,10 decanediol di(meth)acrylate, 1,12 dodecanediol di(meth)acrylate, trimethylolpropane tri(meth)acrylate, 1,2,4-butanetriol tri(meth)acrylate, 1,4-cyclohexanediol di(meth)acrylate, pentaerythritol tri(meth)acrylate, pentaerythritol tetraacrylate, pentaerythritol tetramethacrylate, sorbitol hexa(meth)acrylate, bis[1-(2-(meth)acryloxy)]-p-ethoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers (see e.g. U.S. Pat. No. 4,652,274), and acrylated oligomers (see e.g. U.S. Pat. No. 4,642,126); and vinyl compounds such as styrene, divinyl succinate, divinyl adipate and divinylphthalate; polyfunctional (meth)acrylates comprising urethane, urea or amide groups. Mixtures of two or more of these free radically polymerizable materials can be used if desired.

These ethylenically unsaturated monomers can be employed in the dental composition(s) either alone or in combination with other ethylenically unsaturated monomers.

Monomers comprising a hydroxyl moiety can also be added. Suitable compounds include 2-hydroxyethyl (meth)acrylate (HEMA), 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, dialkylene glycol mono(meth)acrylate, for example, diethylene glycol mono(meth)acrylate, triethylene glycol mono(meth)acrylate, tetraethylene glycol mono(meth)acrylate, polyethylene glycol mono(meth)acrylate, dipropylene glycol mono(meth)acrylate, polypropylene glycol mono(meth)acrylate, and further 1,2- or 1,3- and 2,3-dihydroxypropyl (meth)acrylate, 2-hydroxypropyl-1,3-di(meth)acrylate, 3-hydroxypropyl-1,2-di(meth)acrylate, N-(meth)acryloyl-1,2-dihydroxypropylamine, N-(meth)acryloyl-1,3-dihydroxypropylamine, adducts of phenol and glycidyl (meth)acrylate, for example, 1-phenoxy-2-hydroxypropyl (meth)acrylate, 1-naphthoxy-2-hydroxypropyl (meth)acrylate, bisphenol A diglycidyl (meth)acrylate and the like, 2-hydroxyethyl (meth)acrylate, 2-hydroxypropyl (meth)acrylate and 2,3-dihydroxypropyl (meth)acrylate are particularly preferable.

If desired, mixtures of one or more of these components can be used.

Suitable polymerizable monomers with a urethane moiety also include those having the structure A-(-S1-U—S2-MA)$_n$ with A being a connector element comprising at least one unit, S1 being a spacergroup comprising at least 4 units connected with each other, S2 being a spacergroup comprising at least 4 units connected with each other, the units of A, S1 and S2 being independently selected from CH$_3$—, —CH$_2$—, —O—, —S—, —NR$^1$—, —CO—, —CR$^1$=,

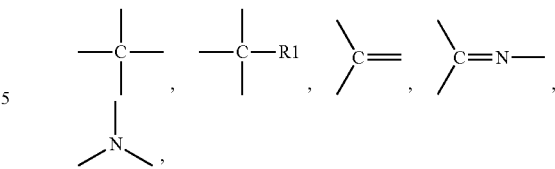

—N=, —CR$^1$R$^2$—, with R$^1$ and R$^2$ independently selected from hydrogen, alkyl, substituted alkyl, alkenyl, cycloalkyl, substituted cycloalkyl, arylalkyl, aryl or substituted aryl, wherein these units can form linear, branched or cyclic structures such as alkyl, cycloalkyl, aryl, ester, urethane or amide groups, U being an urethane, urea or amide group connecting spacergroups S1 and S2, MA being an acrylate or methacrylate group and n being 3 to 6.

Specific examples of polymerizable monomers with urethane moieties include:

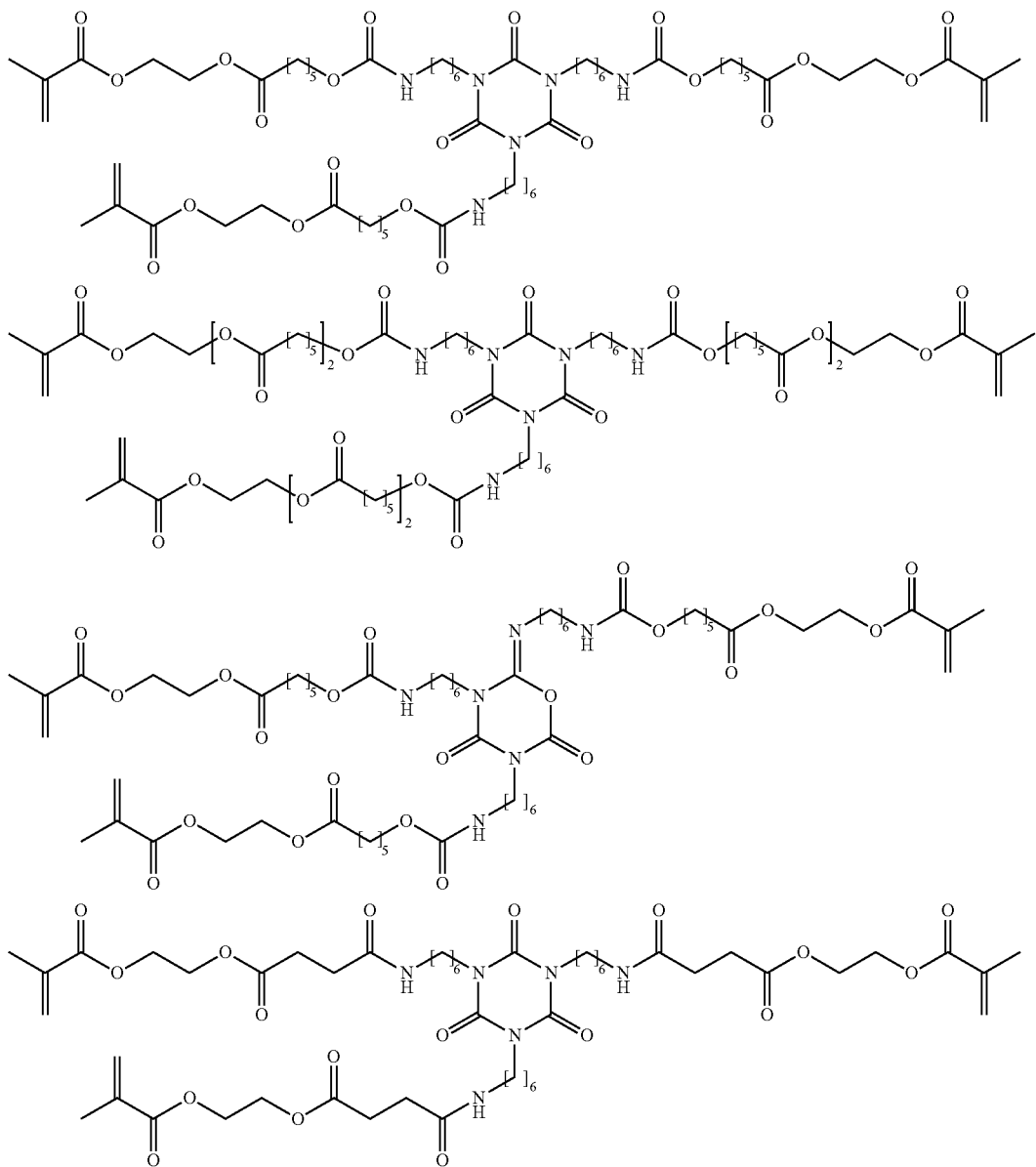

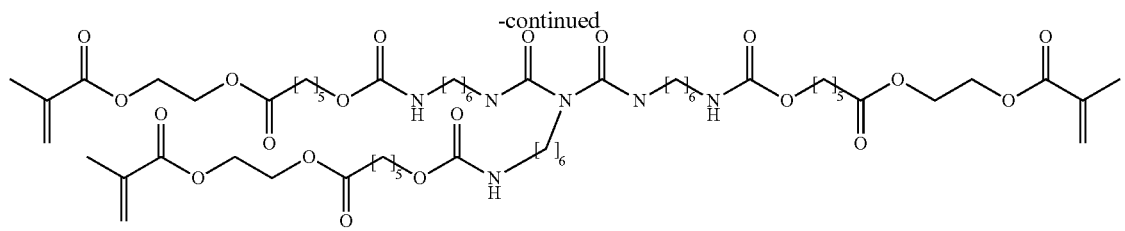

Further examples are described in U.S. Pat. No. 8,329,776 B2 (Hecht et al.). The content of this reference is herewith incorporated by reference.

In addition or besides those components, other hardenable components which can be added include oligomeric or polymeric compounds, such as polyester urethane (meth)acrylates, polyether urethane (meth)acrylates, polycarbonate urethane (meth)acrylates and poly(meth)acrylate urethane (meth)acrylates. The molecular weight of these compounds is typically less than 20,000 g/mol, particularly less than 15,000 g/mol and in particular less than 10,000 g/mol.

Adding these components may be used to adjust the rheological properties.

Mixtures of two, three or more of the polymerizable monomers (3) can be used, if desired.

The polymerizable monomer (2) can be present in the following amounts:

Lower limit: at least about 0 or at least about 1 or at least about 5 wt.-%,
Upper Limit: up to about 70 or up to about 60 or up to about 50 wt.-%,
Range: from about 0 to about 70 or from about 1 to about 60 or from about 5 to about 50 wt.-%, wt.-% with respect to the amount of the whole composition.

The composition described in the present text also comprises an initiator. If more than one initiator component is required, the initiator is also referred to as initiator system.

The nature of the initiator is not particularly limited, unless the desired result cannot be achieved.

The initiator system can comprise systems which are capable of initiating polymerization via radiation (i.e. radiation curing), heat (i.e. heat curing), redox reaction (i.e. redox-curing) or a combination thereof.

A class of initiators capable of initiating polymerization of the hardenable components of the resin matrix which contain free radically active functional groups includes free radical-generating photoinitiators, optionally combined with a photosensitizer or accelerator.

Such initiators typically can be capable of generating free radicals for addition polymerization upon exposure to light energy having a wavelength between about 200 and about 700 nm.

Initiator components which can undergo an alpha-cleavage are sometimes preferred.

Using acylphosphine oxides as initiators or part of the initiator system was found to be particularly useful.

Suitable acylphosphine oxides can be characterized by the following formula $(R^9)_2-P(=O)-C(=O)-R^{10}$ wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a $-Z-C(=O)-P(=O)-(R^9)_2$ group, wherein Z represents a divalent hydrocarbyl group such as alkylene or phenylene having from 2 to 6 carbon atoms.

Suitable systems are also described e.g. in U.S. Pat. No. 4,737,593, the content of which is herewith incorporated by reference.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is 2,4,6-trimethylbenzoyl diphenyl phosphine oxide (Lucirin™ TPO, BASF).

Suitable bisacylphosphine oxides can also be described by the following formula

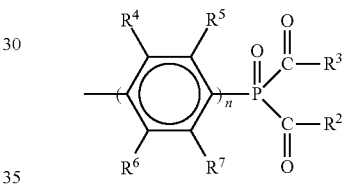

wherein n is 1 or 2, and $R^4$, $R^5$, $R^6$ and $R^7$ are H, C1-4 alkyl, C1-4 alkoxyl, F, Cl or Br; $R^2$ and $R^3$, which are the same or different, stand for a cyclohexyl, cyclopentyl, phenyl, naphthyl, or biphenylyl radical, a cyclopentyl, cyclohexyl, phenyl, naphthyl, or biphenylyl radical substituted by F, Cl, Br, I, C1-4 alkyl and/or C1-4 alkoxyl, or an S or N-containing 5-membered or 6-membered heterocyclic ring; or $R^2$ and $R^3$ are joined to form a ring containing from 4 to 10 carbon atoms and being optionally substituted by 1 to 6 C1-4 alkyl radicals.

More specific examples include: bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-ethoxyphenylphosphine oxide, bis-(2,6-dichlorobenzoyl)-4-biphenylylphosphine oxide, bis-(2,6-dichlorobenzoyl)-4-propylphenylphosphine oxide, bis-(2,6-dichlorobenzoyl)-2-naphthylphosphine oxide, bis-(2,6-dichlorobenzoyl)-1-napthylphosphine oxide, bis-(2,6-dichlorobenzoyl)-4-chlorophenylphosphine oxide, bis-(2,6-dichlorobenzoyl)-2,4-dimethoxyphenylphosphine oxide, bis-(2,6-dichlorobenzoyl)decylphosphine oxide, bis-(2,6-dichlorobenzoyl)-4-octylphenylphosphine oxide, bis-(2,6-dimethoxybenzoyl)-2,5-dimethylphenylphosphine oxide, bis-(2,6-dimethoxybenzoyl)phenylphosphine oxide, bis-(2,4,6-trimethylbenzoyl)-2,5-dimethylphenylphosphine oxide, bis-(2,6-dichloro-3,4,5-trimethoxybenzoyl)-2,5-dimethylphenylphosphine oxide, bis-(2,6-dichloro-3,4,5-trimethoxybenzoyl)-4-ethoxyphenylphosphine oxide, bis-(2-methyl-1-naphthoyl)-2,5-dimethylphenylphosphine oxide, bis-(2-methyl-1-naphthoyl)phenylphosphine oxide, bis-(2-methyl-1-naphthoyl)-4-biphenylylphosphine oxide, bis-(2-methyl- 1-naphthoyl)-4-ethoxyphenylphosphine oxide, bis-(2-methyl-1-naphthoyl)-2-naphthylphosphine oxide, bis-(2-methyl-1-naphthoyl)-4-propylphenylphosphine oxide, bis-(2-methyl-1-naphthoyl)-2,5-dimethylphosphine oxide, bis-(2-methoxy-1-naphthoyl)-4-ethoxyphenylphosphine oxide, bis-(2-methoxy-1-naphthoyl)-4-biphenylylphosphine oxide, bis-(2-methoxy-1-naphthoyl)-2-naphthylphosphine oxide and bis-(2-chloro-1-naphthoyl)-2,5-dimethylphenylphosphine oxide.

The acylphosphine oxide bis(2,4,6-trimethylbenzoyl)phenyl phosphine oxide (IRGACURE™ 819, Ciba Specialty Chemicals, Tarrytown, N.Y.) is sometimes preferred.

Tertiary amine reducing agents may be used in combination with an acylphosphine oxide. Illustrative tertiary amines useful in the invention include ethyl 4-(N,N-dimethylamino)benzoate (EDMAB) and N,N-dimethylaminoethyl methacrylate (DMAEMA).

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis(η5-2,4-cyclopentadien-1-yl)-bis(2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

A variety of visible or near-IR photoinitiator systems may also be used for photopolymerization of free-radically polymerizable materials.

For example, a photoinitiation system can be used selected from systems which initiate polymerization via a two component system of an amine and an α-diketone. Such systems are described e.g. in U.S. Pat. No. 4,071,424 and WO 2009151957, which are herein incorporated by reference.

Alternatively, the resin can be combined with a three components or ternary photoinitiator system. Suitable systems are described in U.S. Pat. No. 5,545,676 and WO 2009151957, which are incorporated herein by reference.

In the ternary photoinitator system, the first component is an iodonium salt, i.e., a diaryliodonium salt. The iodonium salt is preferably soluble in the monomer and shelf-stable (i.e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. No. 3,729,313, U.S. Pat. No. 3,741,769, U.S. Pat. No. 3,808,006, U.S. Pat. No. 4,250,053 and U.S. Pat. No. 4,394,403, the iodonium salt disclosures of which are incorporated herein by reference. The iodonium salt can be a simple salt (e.g., containing an anion such as $Cl^-$, $Br^-$, $I^-$ or $C_4H_5 SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing a julolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula: $ACO(X)_b B$, where X is CO or $CR^5R^6$, where $R^5$ and $R^6$ can be the same or different, and can be hydrogen, alkyl, alkaryl or aralkyl, b is zero or one, and A and B can be the same or different substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incorporated herein by reference.

Another free-radical initiator system that can alternatively be used in the dental compositions described in the present text is the class of ionic dye counterion complex initiators comprising a borate anion and a complementary cationic dye.

Borate salt photoinitiators are described, for example, in U.S. Pat. No. 4,772,530, U.S. Pat. No. 4,954,414, U.S. Pat. No. 4,874,450, U.S. Pat. No. 5,055,372, and U.S. Pat. No. 5,057,393, the disclosures of which are incorporated herein by reference.

Borate anions useful in these photointiators generally can be of the formula $R^1R^2R^3R^4B^-$, wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium.

Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri (2-pyridyl-s-triazine) and related ligands.

Yet another alternative class of initiators capable of initiating polymerization of free radically active functional groups includes conventional chemical initiator systems such as a combination of a peroxide and an activator such as an amine. These initiators, which rely upon a thermal redox reaction, are often referred to as "auto-cure catalysts." They are typically supplied as two-part systems in which the reactants are stored apart from each other and then combined immediately prior to use.

In particular, compounds such as lauroyl peroxide, benzoyl peroxide and p-chlorobenzoyl peroxide and p-methylbenzoyl peroxide can be considered as organic peroxide compounds.

Suitable as activators are, for example, tertiary aromatic amines, such as the N,N-bis-(hydroxyalkyl)-3,5-xylidines known from U.S. Pat. No. 3,541,068 as well as N,N-bis-(hydroxyalkyl)-3,5-di-t-butylanilines, in particular N,N-bis-([beta]-oxybutyl)-3,5-di-t-butylaniline as well as N,N-bis-(hydroxyalkyl)-3,4,5-trimethylaniline.

Well-suited activators are also the barbituric acids and barbituric acid derivatives as described in US 2003/008967, DE 14 95 520 as well as the malonyl sulfamides described in U.S. Pat. No. 4,544,742 (corresponding to EP 0 059 451). Preferred malonyl sulfamides are 2,6-dimethyl-4-isobutylmalonyl sulfamide, 2,6-diisobutyl-4-propylmalonyl sulfamide, 2,6-dibutyl4-propylmalonyl sulfamide, 2,6-dimethyl4-ethylmalonyl sulfamide and 2,6-dioctyl4-isobutyl malonyl sulfamide.

For further acceleration, the polymerization is in this case preferably carried out in the presence of heavy-metal compounds and ionogenic halogen or pseudohalogen. The heavy metal is suitably used in the form of soluble organic compounds. Likewise, the halide and pseudohalide ions are suitably used in the form of soluble salts, as examples there can be named the soluble amine hydrochlorides as well as quarternary ammonium chloride compounds. Suitable accelerators are in particular metals from the iron or copper group, preferably copper and iron complexes and in particular copper complexes. The heavy metal is preferably employed in the form of soluble organic compounds. Suitable are, for example, iron carboxylates, copper carboxylates, iron procetonate, copper procetonate, copper naphthenate, copper acetate and iron naphthenate.

In a further alternative, heat may be used to initiate the hardening, or polymerization, of free radically active groups. Examples of heat sources suitable for the dental materials described in the present text include inductive, convective, and radiant. Thermal sources should be capable of generating temperatures of at least 40° C. to 15° C. This procedure is sometime preferred for initiating polymerization of materials occurring outside of the oral environment.

Yet another alternative class of initiators capable of initiating polymerization of free radically active functional groups that are useful for the dental materials as described in the present text are those that include free radical-generating thermal initiators. Examples include peroxides such as, for example, benzoyl peroxide and lauryl peroxide, and azo compounds such as, for example, 2,2-azobis-isobutyronitrile (AIBN).

If the color of the cured composition matters, an initiator system which does not lead to undesired discoloration should be used. It was found that an initiator system comprising the following components is particularly useful: monoacylphosphine oxides and/or bisacylphosphine oxides. The initiator or initiator system is typically contained in the following amounts:

Lower limit: at least about 0.1 or at least about 0.2 or at least about 0.3 wt.-%, Upper Limit: up to about 10 or up to about 8 or up to about 6 wt.-%, Range: from about 0.1 to about 10 or from about 0.2 to about 8 or from about 0.3 to about 6 wt.-%, wt.-% with respect to the amount of the whole composition.

The composition described in the present text also comprises filler.

Adding a filler can be beneficial e.g. for adjusting the rheological properties like viscosity. The content of the filler also typically influences the physical properties of the composition after hardening, like hardness or flexural strength.

The chemical nature of the filler(s) is not particularly limited unless the intended purpose cannot be achieved.

The size of the filler particles should be such that a homogeneous mixture with the hardenable component forming the resin matrix can be obtained.

The particle size of the filler may be in a range from about 0.001 to about 10 µm.

The filler(s) typically comprise non acid reactive fillers. A non-acid reactive filler is a filler which does not undergo an acid/base reaction with an acid.

Useful non acid reactive fillers include fumed silica, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including the molecular sieves, barium sulphate, yttrium fluoride.

Suitable fumed silicas include for example, products sold under the tradename Aerosil™ series OX-50, -130, -150, and -200, Aerosil R8200 available from Degussa AG, (Hanau, Germany), CAB-O-SIL™ M5 available from Cabot Corp (Tuscola, Ill.), and HDK types, e.g. HDK-H 2000, HDK H15; HDK H18, HDK H2O and HDK H30 available from Wacker.

The average surface area of the silica particles is preferably greater than about 15 $m^2/g$ more preferably greater than about 30 $m^2/g$.

Filler(s) which can also be used include nano-sized fillers such as nano-sized silica.

Suitable nano-sized particles typically have a mean particle size in the range of about 5 to about 80 nm.

Preferred nano-sized silicas are commercially available from Nalco Chemical Co. (Naperville, Ill.) under the product designation NALCO COLLOIDAL SILICAS (for example, preferred silica particles can be obtained from using NALCO products 1040, 1042, 1050, 1060, 2327 and 2329), Nissan Chemical America Company, Houston, Tex. (for example, SNOWTEX-ZL, -OL, -O, -N, -C, -20L, -40, and -50); Admatechs Co., Ltd., Japan (for example, SX009-MIE, SX009-MIF, SC1050-MJM, and SC1050-MLV); Grace GmbH & Co. KG, Worms, Germany (for example, those available under the product designation LUDOX, e.g., P-W50, P-W30, P-X30, P-T40 and P-T40AS); Akzo Nobel Chemicals GmbH, Leverkusen, Germany (for example, those available under the product designation LEVASIL, e.g., 50/50%, 100/45%, 200/30%, 200A/30%, 200/40%, 200A/40%, 300/30% and 500/15%), and Bayer Material-Science AG, Leverkusen, Germany (for example, those available under the product designation DISPERCOLL S, e.g., 5005, 4510, 4020 and 3030).

Surface-treating the nano-sized silica particles before loading into the dental material can provide a more stable dispersion in the resin. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

Thus, the silica particles as well as other suitable non acid-reactive fillers can be treated with a resin-compatibilizing surface treatment agent.

Particularly preferred surface treatment or surface modifying agents include silane treatment agents capable of polymerizing with a resin. Preferred silane treatment agent include gamma-methacryloxylpropyltrimethoxysilane, available commercially under the trade designation A-174, available commercially from Witco OSi Specialties (Danbury, Conn.) and gamma-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, hydroxy alkyl, hydroxy aryl, or amino alkyl functional silanes.

Besides an inorganic material the filler(s) can also be based on an organic material. Examples of suitable organic filler particles include filled or unfilled pulverized polycarbonates, poly(meth)acrylates, polyepoxides, and the like.

If desired, the measurement of the particle size of the filler particles can be done with a TEM (transmission electron microscopy) method, whereby a population is analyzed to obtain an average particle diameter.

A preferred method for measuring the particle diameter can be described is as follows:

Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50-100 particles can be measured and an average diameter is determined.

The amount of filler to be used in the filler matrix usually depends on the purpose for which the composition should be used.

The filler is typically used in the following amounts:
Lower limit: at least about 20 or at least about 30 or at least about 40 wt.-%,
Upper Limit: up to about 95 or up to about 90 or up to about 85 wt.-%,
Range: from about 20 to about 95 or from about 30 to about 90 or from about 40 to about 85 wt.-%,
wt.-% with respect to the amount of the whole composition.

The adhesive composition described in the present text may also comprise additives.

Besides the above mentioned components, the dental composition described in the present text may further contain one, two or more of the following additives:
x-ray visible particles,
pigments,
photobleachable colorants,
fluoride release agents,
stabilizers,
retarders,
and mixtures thereof.

Suitable x-ray visible particles which may be present include particles of metal oxides like the oxides of yttrium, ytterbium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72 are optionally included in the materials of the invention. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof.

Examples of pigments, which can be used include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual coloring of the dental compositions.

Examples of photobleachable colorants which can be present include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725. The color of the compositions of the invention may be additionally imparted by a sensitizing compound.

Examples of fluoride release agents which can be present include naturally occurring or synthetic fluoride minerals. These fluoride sources can optionally be treated with surface treatment agents.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole,
phenothiazine, and HALS (hindered amine light stabilizers).

Further additives, which can be added, include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl) adipate), tricresyl phosphate, paraffin oils, glycerol triacetate, bisphenol A diacetate, ethoxylated bisphenol A diacetate, and silicone oils), flavorants, anti-microbials, fragrance, agents that impart fluorescence and/or opalescence and fluoride releasing materials.

There is no need for the additive(s) to be present. The additive(s) may be present in the following amounts:
Lower limit: at least about 0 or at least about 0.1 or at least about 1 wt.-%,
Upper Limit: up to about 10 or up to about 8 or up to about 5 wt.-%,
Range: from about 0 to about 10 or from about 0.1 to about 8 or from about 1 to about 5 wt.-%,
wt.-% with respect to the amount of the whole composition.

According to a further embodiment, the dental composition described in the present text is described as follows:
Polymerizable monomer (1): from about 1 to about 75 wt.-%, or from about 5 to about 70 wt.-%, or from about 10 to about 65 wt.-%;
Polymerizable monomer (2): from about 0 to about 60 wt.-%, or from about 0.1 to about 50 wt.-%, or from about 1 to about 40 wt.-%;
Polymerizable monomer (3): from 0 to about 70 wt.-%, or from about 1 to about 60 wt.-%, or from about 5 to about 50 wt.-%;
Initiator(s): from about 0.1 to about 10 wt.-%, or from about 0.2 to about 8 wt.-%, or from about 0.3 to about 6 wt.-%;
Filler(s): from about 20 to about 95 wt.-%, or from about 30 to about 90 wt.-%, or from about 40 to about 85 wt.-%;
Additive(s): from 0 to about 10 wt.-%, or from about 0.1 to about 8 wt.-%, or from about 1 to about 5 wt.-%;
wt.-% with respect to the weight of the whole composition.

The dental composition described in the present text can be produced as follows:
providing the respective components,
mixing the components.

Mixing can be achieved by using any means known to the practitioner. That is, the adhesive composition can be prepared in an one-pot synthesis simply by putting the respective components together and mixing them.

If desired, the production process is performed under save light conditions to avoid an undesired polymerization of the composition.

The hardenable dental composition described in the present text is typically stored in a container until use. Depending on the formulation and the curing status, various containers can be used.

The composition can be provided in the form of a one-component system or as a two-component system. This typically depends on the initiator system chosen. If the composition is redox curable or curing, it is usually provided as a two-component system.

If the dental composition is provided as a one-component system, it can be stored in a container having only one chamber such as a compule or screw tube.

A compule typically has a cylindrical housing with a front and a rear end and a nozzle. The rear end of the housing is usually sealed with a movable piston. Typically, the dental composition is dispensed out of the compule or container using an applier having a movable plunger (e.g. an application device having the shape of a caulk gun). Examples of suitable compules or containers are described in U.S. Pat. No. 5,624,260, EP 1 340 472 A1, US 2007/0172789 A1, U.S. Pat. No. 5,893,714 and U.S. Pat. No. 5,865,803, the content of which with regard to the description of compules or containers is herewith incorporated by reference.

Suitable two-component systems for storage include two-barrel cartridges.

Suitable two-component systems are described e.g. in US 2007/0090079 or U.S. Pat. No. 5,918,772. The content of these documents with respect to the description of the vial or bottle is herewith incorporated by reference. Cartridges which can be used are also commercially available from SulzerMixpac AG (Switzerland).

The volume of each compartment of the two-barrel cartridges is typically in the range from about 0.1 to about 100 ml or from about 0.5 to about 50 ml or from about 1 to about 30 ml.

The volume ratio of compartment (I) to compartment (II) is typically within a range of about 1:1 to about 10:1.

Static mixing tips which can be used for mixing the compositions contained in the compartments are described e.g. in US 2006/0187752 or in U.S. Pat. No. 5,944,419. The disclosure of these patents is herewith incorporated by reference. Mixing tips which can also be used are commercially available from SulzerMixpac AG (Switzerland).

If the dental composition is provided in the form of a dental mill blank, it is typically fixed to a holding device including frames or mandrels.

The invention described in the present text is also directed to a kit of parts.

Such a kit typically comprises the dental composition described in the present text, a dental adhesive and/or a dental cement, optionally an applicator and optionally an instruction of use.

The instruction of use typically contains hints to the practitioner how and under what conditions the adhesive composition should be applied to the surface of hard dental tissue.

The dental composition can be used as or for producing a dental filling material, dental cement, dental crown or bridge material or dental mill blank.

The dental composition is typically used in the mouth of a patient and is disposed adjacent to natural teeth. The phrase "disposed adjacent to" as used herein refers to the placing of a dental material in temporary or permanent (e.g., occlusal or proximal) contact with a natural tooth.

The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth.

A typical application process for the composition described in the present text to be used as a restorative composite typically includes the following steps in the desired order:
providing the composition,
placing the composition in contact with hard dental tissue, especially the surface thereof,
curing the composition, e.g. by applying radiation (e.g. visible light) to the composition for a period of time sufficient to initiate the polymerisation process (e.g. about 5 to about 20 s).

Suitable tools for applying radiation include dental curing lights. Suitable dental curing lights are described e.g. in US 2005/0236586. The content of this document is herewith incorporated by reference. Suitable dental curing lights are also commercially available e.g. under the trade names Elipar™ S10 (3M ESPE).

The dental composition described in the present text can also be used for producing a dental crown, bridge, onlay or inlay outside the mouth of a patient.

The production can be done either by a so-called constructive approach (i.e. build-up approach) or by a so-called destructive approach (i.e. machining or milling approach).

The build-up approach can be performed by any means known to the skilled person including rapid-prototyping techniques.

Rapid-prototyping techniques include ink jet printing, 3d-printing, robo-casting, laminated object manufacturing, stereolithography, photostereolithography, or combinations thereof.

A suitable example for a suitable process is described e.g. in US 2012/068388 (3M). The content of this reference is herewith incorporated by reference.

The machining approach can also be performed by any means known to the skilled person including milling the desired dental restoration out of a dental mill blank.

If desired, the dental mill blank can be attached to a holding device. Suitable holding devices include frames and stubs or mandrels. Sometimes it can be desirable, if the dental mill blank is put in a magazine, either for storing or for machining. The holding device typically facilitates the machining of the dental article, e.g. by using a machining or milling device.

Examples of holding devices are shown in US 2003/0132539, U.S. Pat. No. 6,769,912 and EP 0 455 854 B1. The content of these documents with regard to holding devices (e.g. frames and stubs or supporting body) is herewith incorporated by reference and regarded part of the text of the present invention.

Fixing of the dental mill blank to the holding device can be achieved e.g. by gluing. The fixing should be such that the dental milling blank can be processed in a milling machine.

Besides gluing other means for attaching the holding device include bonding, screwing, and combinations thereof.

Thus, a further embodiment of the present invention is directed to a process for producing a dental mill blank, the process comprising the steps of
providing a dental composition as described in the present text, the dental composition being in its uncured state,
hardening or curing the dental composition to obtain a hardened or cured dental composition,
optionally fixing the hardened dental composition to a holding device,
the dental composition being provided in the shape of a dental mill blank.

The dental mill blank can be produced by placing the curable dental composition into a mould followed by a curing step.

Another option for producing a dental mill blank is to apply a build-up or layer technique. In that case, the dental composition is typically provided in the form of a flat layer, the layer is cured and a further curable layer of the dental composition is applied on top of the previous layer followed by a further curing step. These steps are repeated until the object has the desired dimensions.

Yet, a further embodiment of the present invention is directed to a process for producing a dental restoration, the process comprising the steps of
providing a dental mill blank as described in the present text, the dental mill blank comprising the dental composition described in the present text, the dental composition being in its cured state,
machining the dental mill blank to obtain a dental restoration, the dental restoration having typically the shape of a dental crown, bridge, inlay or veneer.

According to a particular embodiment, the dental composition described in the present text is characterized as follows:
Polymerizable monomer(s) (1) being represented by a formula as described in the text above with respect to the polymerizable monomer (1) in an amount from about 1 to about 75 wt.-%,
Initiator(s) being selected from radiation curing or redox curing initiators,
Silica or silica/zirconia filler(s) from about 20 to about 95 wt.-%.

All components used in the dental composition of the invention should be sufficiently biocompatible, that is, the composition should not produce a toxic, injurious, or immunological response in living tissue.

According to one embodiment, the dental composition described in the present text does not contain or is essentially free of either or more or all of the following components:
Solvent(s) selected from water or alcohol(s) (e.g. ethanol) or combinations thereof in an amount of more than about 5 or 10 or 20 wt.-%, wt.-% with respect to the weight of the whole composition.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

EXAMPLES

Unless otherwise indicated, all parts and percentages are on a weight basis, all water is deionized water, and all molecular weights are weight average molecular weight. Moreover, unless otherwise indicated all Experiments were conducted at ambient conditions (23° C.; 1013 mbar). Moreover, nearly all process steps are conducted under an atmosphere of dry air:

Compressive Strength 1 (CS 1)

If desired, the measurement of the compressive strength 1 can be carried out according to ISO 4049 using specimens having the dimension of 3 mm×3 mm×5 mm. The compressive strength 1 is typically given in MPa.

Compressive Strength 2 (CS 2)

If desired, the measurement of the compressive strength 2 can be carried out according to DIN 53454 (ISO 9917 2001) using cylindrical specimens with a diameter of 4 mm and a height of 8 mm. The compressive strength 2 is typically given in MPa.

Abbreviations

The name and/or structure of the components used are given in Table 1.

TABLE 1

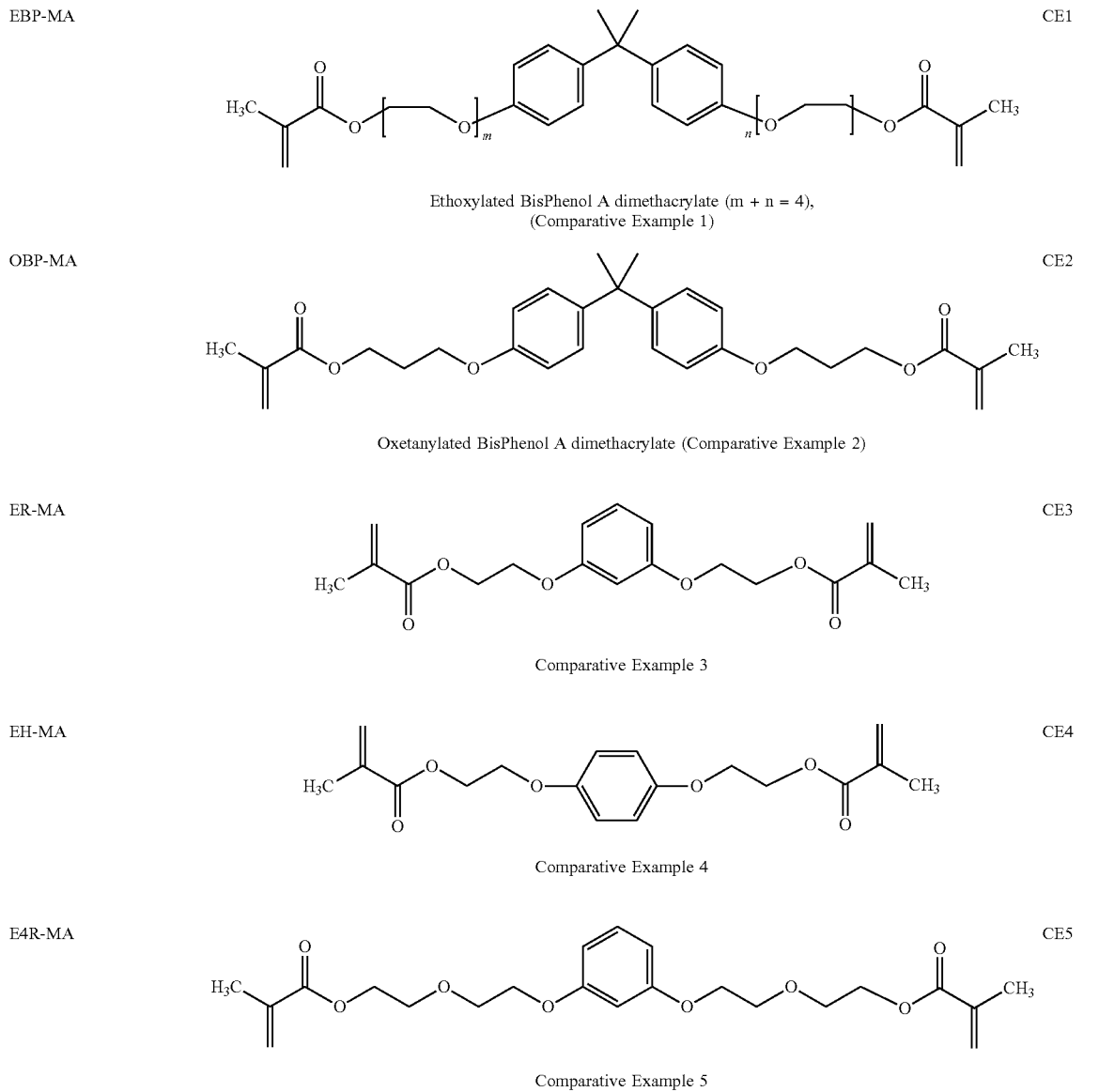

EBP-MA — Ethoxylated BisPhenol A dimethacrylate (m + n = 4), (Comparative Example 1) — CE1

OBP-MA — Oxetanylated BisPhenol A dimethacrylate (Comparative Example 2) — CE2

ER-MA — Comparative Example 3 — CE3

EH-MA — Comparative Example 4 — CE4

E4R-MA — Comparative Example 5 — CE5

TABLE 1-continued

OR-MA

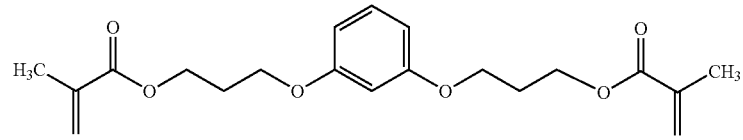 [SMILES: C=C(C)C(=O)OCCCOc1cccc(OCCCOC(=O)C(=C)C)c1]

Comparative Example 6

CE6

EER-A/MA/AM

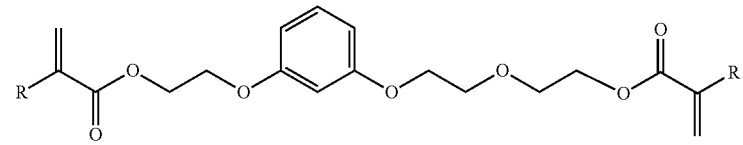

R = H: EER-A, R = CH3: EER-MA (Inventive Example 1),
R = 1x H/1x CH3: EER-AM

IE1

EOR-A/MA/AM

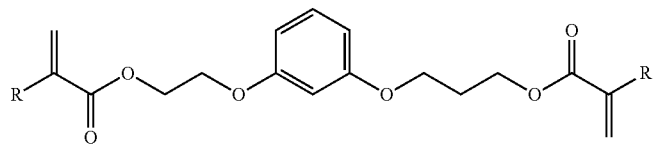

R = H: EOR-A, R = CH3: EOR-MA, R = 1x H/1x CH3: EOR-AM

OER-A/MA/AM

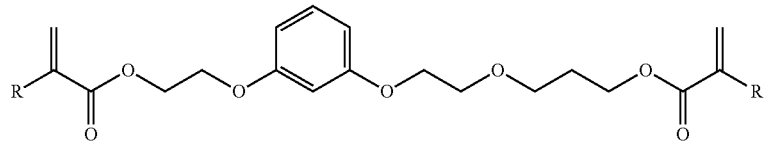

R = H: OER-A, R = CH3: OER-MA (Inventive Example 2),
R = 1x H/1x CH3: OER-AM

IE2

OOR-A/MA/AM

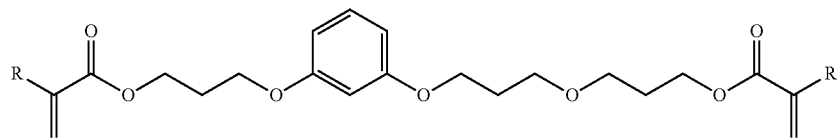

R = H: OOR-A, R = CH3: OOR-MA (Inventive Example 3),
R = 1x H/1x CH3: OOR-AM

IE3

OE2R-A/MA/AM

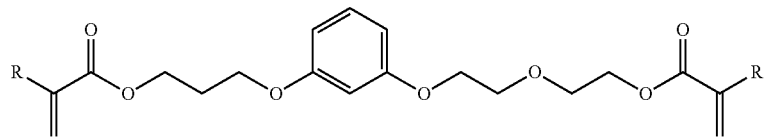

R = H: OE2R-A, R = CH3: OE2R-MA (Inventive Example 4),
R = 1x H/1x CH3: OE2R-AM

IE4

HOR-A/MA/AM

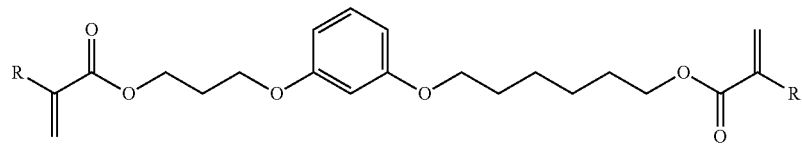

R = H: HOR-A, (Inventive Example 6), R = CH3: HOR-MA
(Inventive Example 5), R = 1x H/1x CH3: HOR-AM

IE5,
IE6

TABLE 1-continued

POR-A/MA/AM

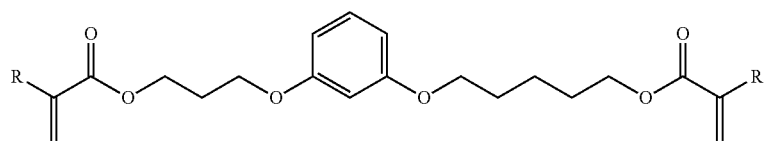

R = H: POR-A, R = CH3: POR-MA (Inventive Example 7),
R = 1x H/1x CH3: POR-AM

IE7

EEC-A/MA/AM

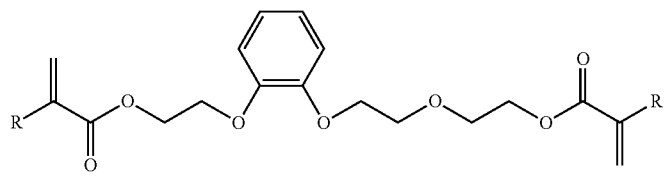

R = H: EEC-A, R = CH3: EEC-MA, R = 1x H/1x CH3: EEC-AM

OE2C-A/MA/AM

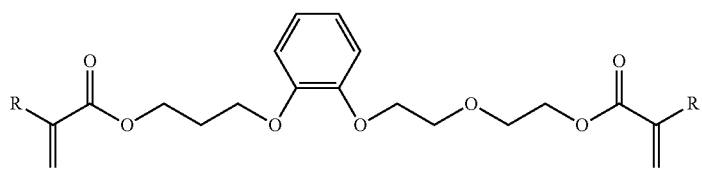

R = H: OE2C-A, R = CH3: OE2C-MA (Inventive Example 8),
R = 1x H/1x CH3: OE2C-AM

IE8

E4RE-A/MA/AM

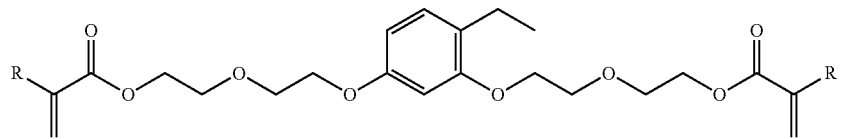

R = H: E4RE-A, R = CH3: E4RE-MA (Inventive Example 9),
R = 1x H/1x CH3: E4RE-AM

IE9

E4RH-A/MA/AM

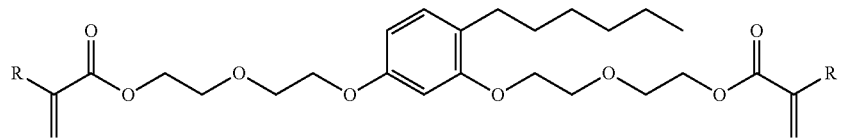

R = H: E4RH-A, R = CH3: E4RH-MA (Inventive Example 10),
R = 1x H/1x CH3: E4RH-AM

IE10

ORE-A/MA/AM

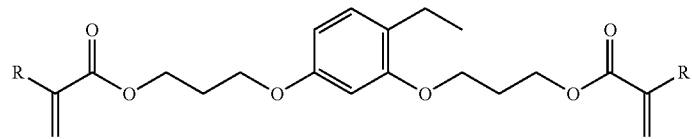

R = H: ORE-A, R = CH3: ORE-MA (Inventive Example 11),
R = 1x H/1x CH3: ORE-AM

IE11

ORH-A/MA/AM

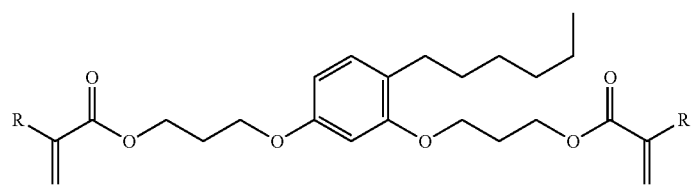

R = H: ORH-A, R = CH3: ORH-MA (Inventive Example 12),
R = 1x H/1x CH3: ORH-AM

IE12

TABLE 1-continued

EBC-A/MA/AM

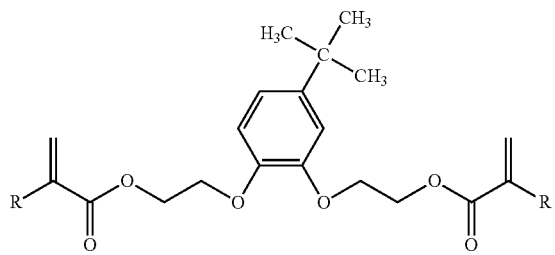

R = H: EBC-A, R = CH3: EBC-MA (Inventive Example 13),
R = 1x H/1x CH3: EBC-AM

IE13

EEBC-A/MA/AM

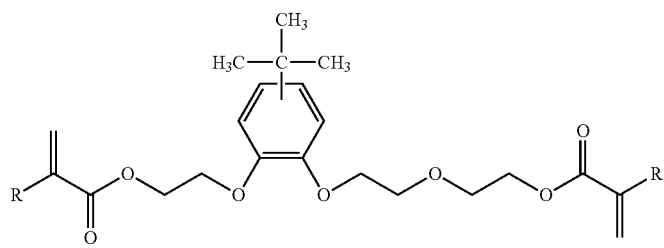

R = H: EEBC-A, R = CH3: EEBC-MA (Inventive Example 14),
R = 1x H/1x CH3: EEBC-AM

IE14

E4BC-A/MA/AM

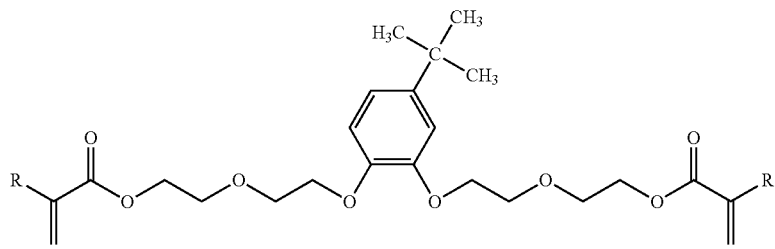

R = H: E4BC-A, R = CH3: E4BC-MA (Inventive Example 15),
R = 1x H/1x CH3: E4BC-AM

IE15

OBC-A/MA/AM

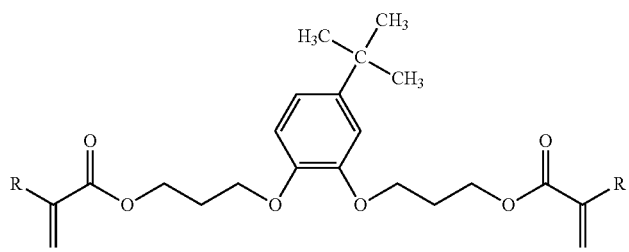

R = H: OBC-A, R = CH3: OBC-MA (Inventive Example 16),
R = 1x H/1x CH3: OBC-AM

IE16

OE2BC-A/MA/AM

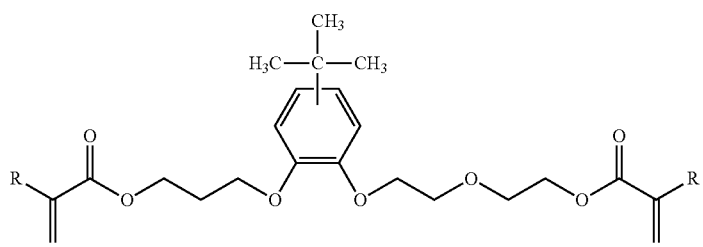

R = H: OE2BC-A, R = CH3: OE2BC-MA (Inventive Example 17),
R = 1x H/1x CH3: OE2BC-AM

IE17

TABLE 1-continued
BC-GA/MA/AM 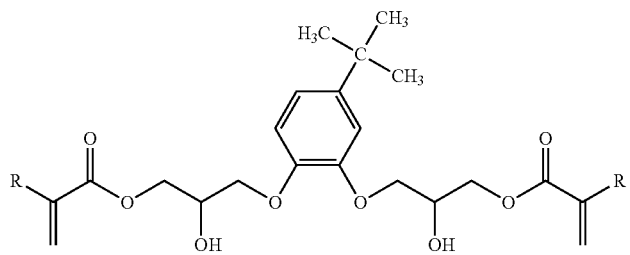 IE18
R = H: BC-GA, R = CH3: BC-GMA (Inventive Example 18),
R = 1x H/1x CH3: BC-GAM
PGS-A/MA/AM 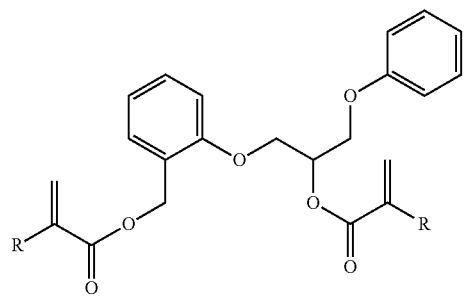
R = H: PGS-A, R = CH3: PGS-MA, R = 1x H/1x CH3: PGS-AM
PGiS-A/MA/AM 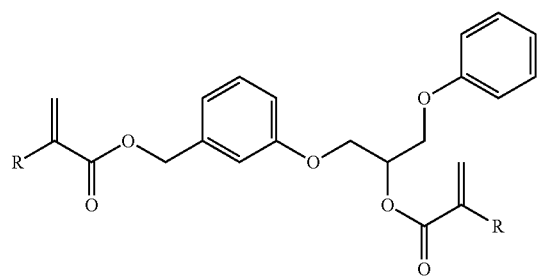
R = H: PGiS-A, R = CH3: PGiS-MA, R = 1x H/1x CH3: PGiS-AM
PGT-A/MA/AM 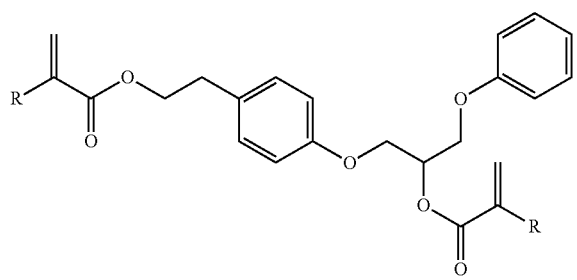 IE19
R = H: PGT-A, R = CH3: PGT-MA, R = 1x H/1x CH3: PGT-AM
(Inventive Example 19)
EGS-A/MA/AM 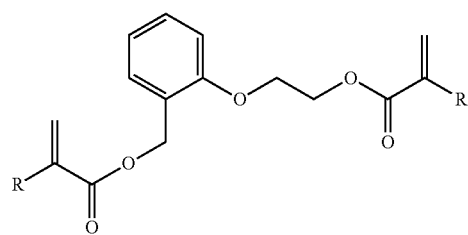
R = H: EGS-A, R = CH3: EGS-MA, R = 1x H/1x CH3: EGS-AM TABLE 1-continued
EGiS-A/MA/AM
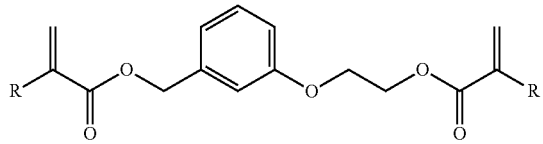
R = H: EGiS-A, R = CH3: EGiS-MA, R = 1x H/1x CH3: EGiS-AM
ET-A/MA/AM
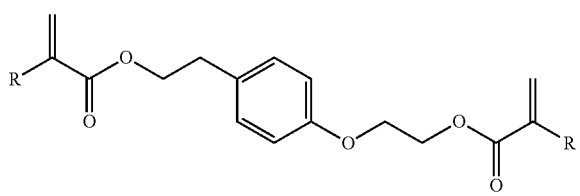
IE20
R = H: ET-A, R = CH3: ET-MA (Inventive Example 20),
R = 1x H/1x CH3: ET-AM
E2GS-A/MA/AM
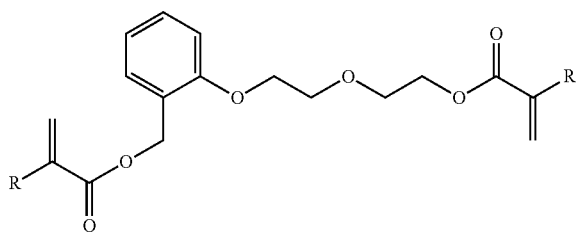
R = H: E2GS-A, R = CH3: E2GS-MA, R = 1x H/1x CH3: E2GS-AM
E2GiS-A/MA/AM
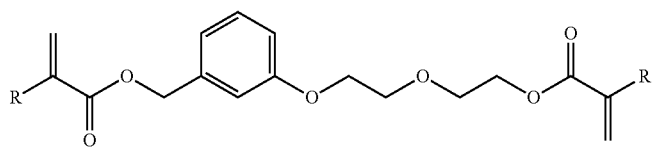
R = H: E2GiS-A, R = CH3: E2GiS-MA, R = 1x H/1x CH3: E2GiS-AM
E2T-A/MA/AM
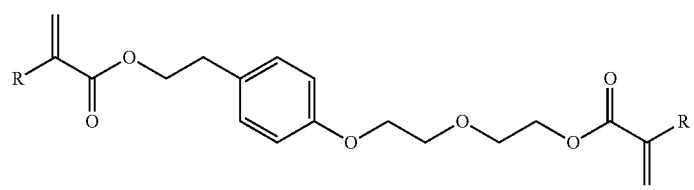
IE21
R = H: E2T-A, R = CH3: E2T-MA (Inventive Example 21),
R = 1x H/1x CH3: E2T-AM
OGS-A/MA/AM
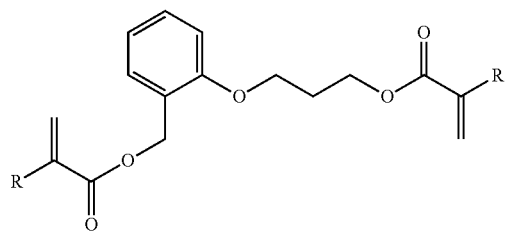
R = H: OGS-A, R = CH3: OGS-MA, R = 1x H/1x CH3: OGS-AM TABLE 1-continued
OGiS-A/MA/AM
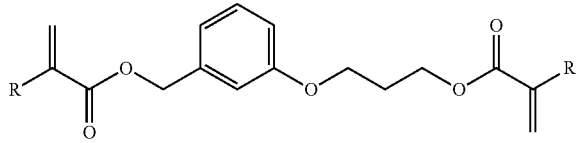
R = H: OGiS-A, R = CH3: OGiS-MA, R = 1x H/1x CH3: OGiS-AM
OT-A/MA/AM
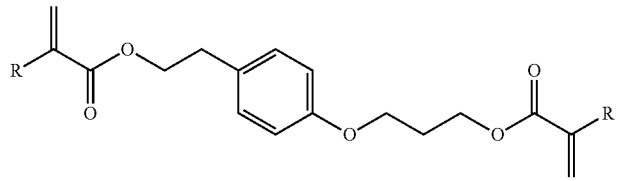
R = H: OT-A, R = CH3: OT-MA (Inventive Example 22),
R = 1x H/1x CH3: OT-AM
IE22
MGS-A/MA/AM
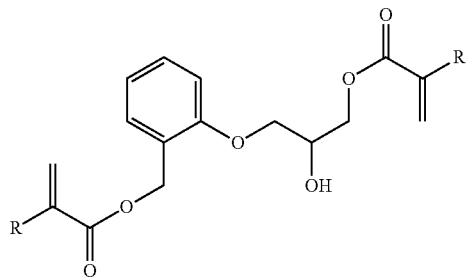
R = H: MGS-A, R = CH3: MGS-MA, R = 1x H/1x CH3: MGS-AM
MGiS-A/MA/AM
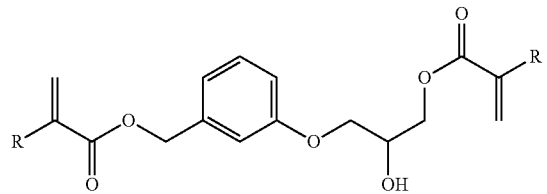
R = H: MGiS-A, R = CH3: MGiS-MA, R = 1x H/1x CH3: MGiS-AM
MGT-A/MA/AM
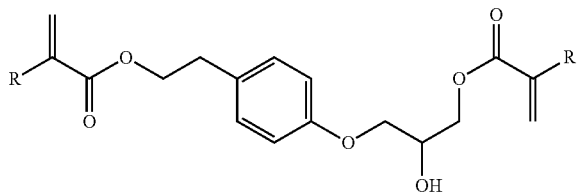
R = H: MGT-A, R = CH3: MGT-MA (Inventive Example 23),
R = 1x H/1x CH3: MGT-AM
IE23
O2oHB-A/MA/AM
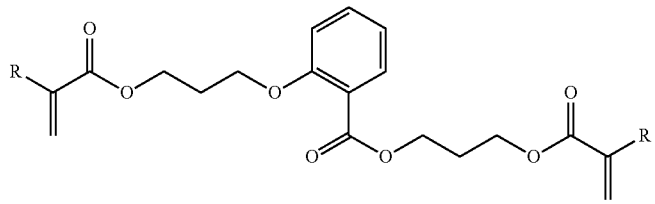
R = H: O2oHB-A, R = CH3: O2oHB-MA, R = 1x H/1x CH3: O2oHB-AM TABLE 1-continued
OE2oHB-A/MA/AM
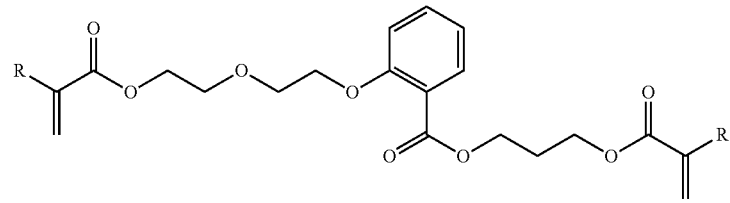
R = H: OE2oHB-A, R = CH3: OE2oHB-MA, R = 1x H/1x CH3: OE2oHB-AM
E4oHB-A/MA/AM
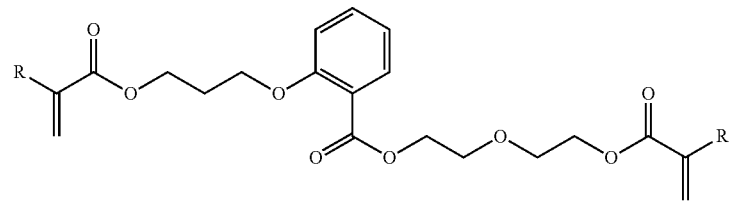
R = H: E4oHB-A, R = CH3: E4oHB-MA, R = 1x H/1x CH3: E4oHB-AM
O2mHB-A/MA/AM
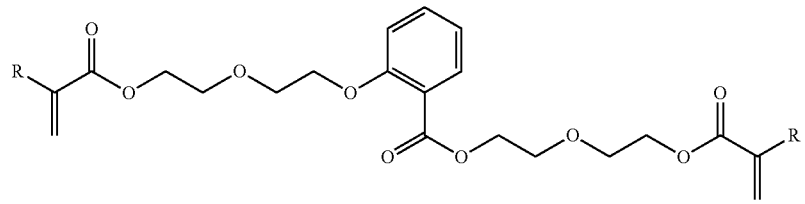
R = H: O2mHB-A, R = CH3: O2mHB-MA, R = 1x H/1x CH3: O2mHB-AM
OE2mHB-A/MA/AM
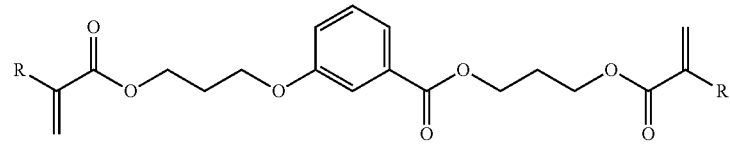
and
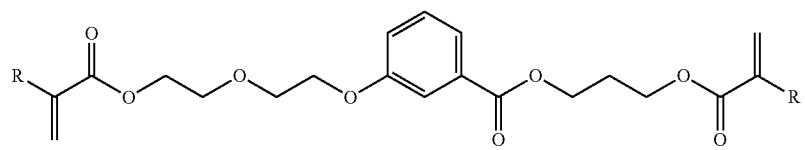
R = H: OE2mHB-A, R = CH3: OE2mHB-MA, R = 1x H/1x CH3: OE2mHB-AM
E4mHB-A/MA/AM
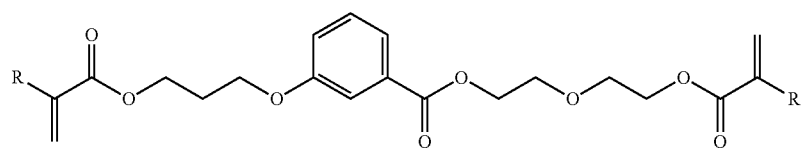
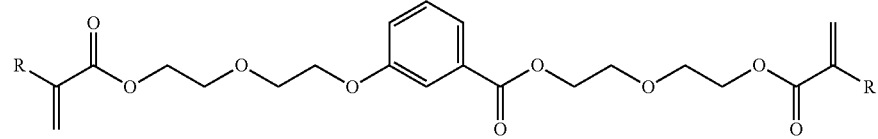
R = H: E4mHB-A, R = CH3: E4mHB-MA, R = 1x H/1x CH3: E4mHB-AM

TABLE 1-continued

O2pHB-A/MA/AM

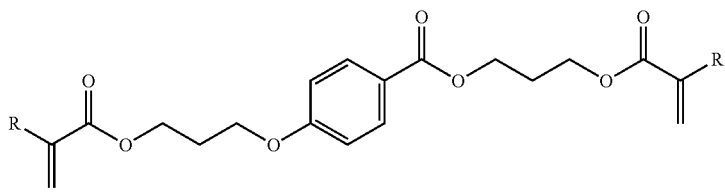

R = H: O2pHB-A, R = CH3: O2pHB-MA, R = 1x H/1x CH3: O2pHB-AM

OE2pHB-A/MA/AM

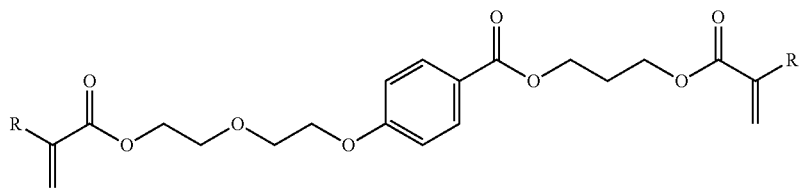

and

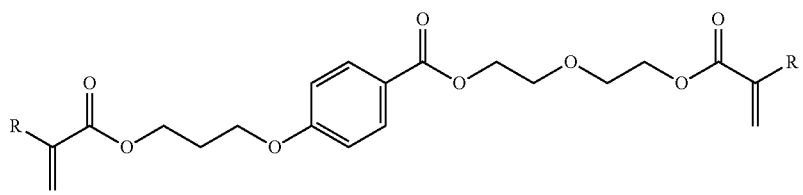

R = H: OE2pHB-A, R = CH3: OE2pHB-MA, R = 1x H/1x CH3: OE2pHB-AM

E4pHB-A/MA/AM

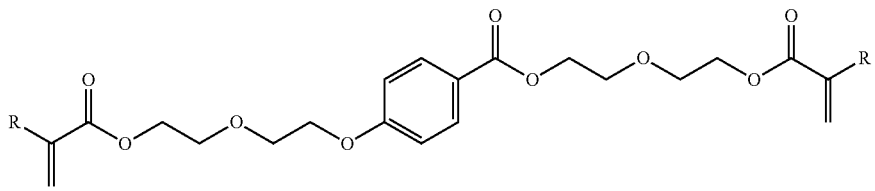

R = H: E4pHB-A, R = CH3: E4pHB-MA, R = 1x H/1x CH3: E4pHB-AM

| | | |
|---|---|---|
| Resorcinol | 1,3-dihydroxybenzene, CAS 108-46-3, EC 203-585-2 | R |
| Catechol | 1,2-dihydroxybenzene, CAS 120-80-9, EC 204-427-5 | C |
| Tert-butylcatechol | 4-tert-butylcatechol, 4-tert-butyl-1,2-dihydroxybenzene, CAS 98-29-3, EC 202-653-9 | BC |
| Tyrosol | 4-(2-hydroxyethyl)phenol, 2-(4-hydroxyphenyl)ethanol, CAS 501-94-0, EC 207-930-8 | T |
| Salicyl alcohol | 2-hydroxybenzyl alcohol, 2-hydroxymethylphenol, Saligenin, CAS 90-01-7, EC 201-960-5 | S |
| iso-Salicyl alcohol | 3-hydroxybenzyl alcohol, 3-hydroxymethylphenol, CAS 620-24-6, EC 210-633-6 | iS |
| Resorcinol monoacetate | 3-hydroxyphenyl acetate, CAS 102-29-4, EC 203-022-0 | RAc |
| Resorcinol diacetate | 1,3-diacetoxybenzene, CAS 108-58-7, EC 203-596-2 | RAc2 |
| ortho-Hydroxybenzoic Acid | Salicylic acid, 2-hydroxybenzoic acid, CAS 69-72-7, EC 200-712-3 | oHB |
| meta-Hydroxybenzoic Acid | Iso-Salicylic acid, 3-hydroxybenzoic acid, CAS 99-06-9, EC 202-726-5 | mHB |
| para-Hydroxybenzoic Acid | 4-hydroxybenzoic acid, CAS 99-96-7, EC 202-804-9 | pHB |
| 2-chloroethanol | Ethylene chlorohydrin, CAS 107-07-3, EC 203-459-7 | |
| 3-chloro-1-propanol | 1-chloro-3-hydroxypropane, CAS 627-30-5, EC 210-992-9 | |
| 2-(2-chloroethoxy)ethanol | 3-oxa-5-chloro-1-pentanol, CAS 628-89-7, EC 211-059-9 | |
| 5-chloro-1-pentanol | Pentamethylene chlorohydrin, CAS 5259-98-3, EC 226-067-8 | |
| 6-chloro-1-hexanol | Hexamethylene chlorohydrin, CAS 2009-83-8, EC 217-925-2 | |
| Ethylene carbonate | 1,3-Dioxolan-2-one, CAS 96-49-1, EC 202-510-0 | |
| Glycidyl phenyl ether | 2-(phenoxymethyl)oxirane, 2,3-epoxypropyl phenyl ether, phenyl glycidyl ether, CAS 122-60-1, EC 204-557-2 | GP |
| Glycidyl methacrylate | 2,3-Epoxypropyl methacrylate, Methacrylic acid 2,3-epoxypropyl ester, CAS 106-91-2, EC 203-441-9 | GMA |

TABLE 1-continued

| | | |
|---|---|---|
| Acrylic acid | Propenoic acid, CAS 79-10-7, EC 201-177-9 | AA |
| Methacrylic acid | 2-Methacrylic acid, 2-Methylpropenoic acid, CAS 79-41-4, EC 201-204-4 | MA |
| Methanesulfonic acid | CAS 75-75-2, EC 200-898-6 | MSA |
| Tetrahydrofuran | CAS 109-99-9, EC 203-726-8 | THF |
| iso-Propanol | 2-propanol, CAS 67-63-0, EC 200-661-7 | IPA |
| tert-Butanol | 2-methyl-2-propanol, CAS 75-65-0, EC 200-889-7 | HOtBu |
| Potassium tert-butoxide | Potassium tert-butylate, CAS 865-47-4, EC 212-740-3 | KOtBu |
| Sodium hydroxide | CAS 1310-73-2, EC 215-185-5 | NaOH |
| Potassium hydroxide | CAS 1310-58-3, EC 215-181-3 | KOH |
| Methyl tert-butyl ether | tert-Butyl methyl ether, CAS 1634-04-4, EC 216-653-1 | MTBE |
| Ethyl acetate | Acetic acid ethyl ester, CAS 141-78-6, EC 205-500-4 | EA |
| Methyl ethyl ketone | Ethyl methyl ketone, 2-butanone, CAS 78-93-3, EC 201-159-0 | MEK |
| 2,6-di-tert-Butyl-4-methylphenol | 2,6-Di-tert-butyl-p-cresol, Butylated hydroxytoluene, Butylhydroxytoluene, DBPC, CAS 128-37-0, EC 204-881-4 | BHT |
| hydroquinone | 1,4-dihydroxybenzene, 1,4-benzenediol, CAS 123-31-9, EC 204-617-8 | HQ |
| Hydroquinone monomethyl ether | 4-methoxyphenol, 4-Hydroxyanisole, 4-MP, HQMME, MEHQ, MQ-F, CAS 150-76-5, EC 205-769-8 | HQME |
| Methylene blue | 3,7-bis(Dimethylamino)phenazathionium chloride, Basic Blue 9, Tetramethylthionine chloride, CAS 7220-79-3, EC 200-515-2 | |
| Sodium carbonate | CAS 497-19-8, EC 207-838-8 | Na2CO3 |
| Potassium carbonate | CAS 584-08-7, EC 209-529-3 | K2CO3 |
| DESMA | Urethane methacrylate, cf. Example 1 on page 35 of WO 2009/006282 | Co1 |
| BA2EO-Ac | BisPhenol A ethoxylated, diacetate (CAS no. 19224-29-4) | Sof1 |
| Filler 1 | Non agglomerated silanized silica nano filler, (50 nm); produced according to U.S. Pat. No. 6,899,948 B2 | F1 |
| Filler 2 | Aggregated Zr/Si nanoclusters; produced as described in U.S. Pat. No. 6,730,156, column 25, preparatory example A; surface treated according to process as described in preparatory example B. | F2 |
| Filler 3 | Ground strontium containing glass filler, <3μm (Schott Glaswerke), surface treated | F3 |
| Filler 4 | Fumed silica (Wacker HDKH 2000) | F4 |
| BZPBS | 1-Benzyl-5-phenyl-barbituric acid | Ini1 |
| TBPIN | tert-Butylperoxy-3,5,5-trimethylhexanoate | Ini2 |
| Initiator 3 | Dibutylphenylethylammonium chloride | Ini3 |
| Initiator 4 | Copper(II) bis(1-phenylpentan-1,3-dione) complex | Ini4 |
| CPQ | Camphorquinone (CAS no. 10373-78-1) | Ini5 |
| DPI-PF6 | Diphenyliodonium hexafluorophosphate (CAS no. 58109-40-3) | Ini6 |
| EDMAB | Ethyl 4-dimethylaminobenzoate (CAS no. 10287-53-3) | Ini7 |
| Triphenyl-phosphane | Triphenylphosphine, CAS no. 603-35-0, EC 210-036-0 | PPh3 |
| Triethylamine | CAS no. 121-44-8, EC 204-469-4 | TEA |

General Procedure A: Synthesis of Diol Precursors (e.g. OR or E2T) Via Etherification of Dihydroxybenzenes (e.g. Resorcinol) or Hydroxyalkylphenols (e.g. Tyrosol) Hydroxybenzoic Acids (e.g. mHB) or Via Nucleophilic Esterification of Hydroxybenzoic Acids (e.g. mHB) with Halogenated Alcohols (e.g. 3-Chloro-1-propanol)

To a solution of the corresponding Dihydroxybenzene or Hydroxyalkylphenol and the corresponding Halogenated Alcohol/s in water an aqueous solution of alkaline hydroxide (e.g. NaOH) or alkaline carbonate (e.g. Na2CO3) or ammonia is added at reflux. Optionally the synthesis can be done under a protective gas atmosphere (e.g. nitrogen).

Alternatively IPA or tBuOH can be used as solvent and solid alkaline hydroxide (e.g. KOH) or alkaline carbonate (e.g. Na2CO3) as base.

Also a subsequent reaction pattern is possible for Dihydroxybenzenes or Dihydroxybenzene Monoesters (e.g. RAc) where in the first reaction step one equivalent of base and one half of the Halogenated Alcohol/s is reacted with the Dihydroxybenzene or Dihydroxybenzene Monoester and afterwards in the second reaction step another equivalent of base and the remaining half of the Halogenated Alcohol/s is reacted (if a Dihydroxybenzene Monoester is used then after the first reaction step an ester hydrolysis, e.g. a basic ester hydrolysis, has to be done before the second reaction step can occur).

After stirring over night at reflux the reaction mixture is cooled to room temperature, and the reaction mixture is extracted (e.g. MTBE or EA or MEK) if water is used as solvent. Optionally the reaction mixture can be extracted as it is or the organic phase can be separated and only the aqueous phase can be extracted, afterwards the organic phase is combined with the extracts. Optionally the combined organic phases can be extracted with aqueous alkaline (e.g. NaOH) solutions and/or aqueous acid (e.g. H2SO4) solutions and/or water.

If IPA or tBuOH is used as solvent the reaction mixture is first filtered to remove the precipitate, then the solvent is stripped off in vacuo, and then the residue is extracted against water as described above.

If a Hydroxybenzoic Acid is used as building block first the reaction mixture is acidified with aqueous acid (e.g H2SO4) and then extracted against water as described above to isolate the etherification product Hydroxyalkoxybenzoic Acid and/or the nucleophilic esterification product Hydroxybenzoic Acid Hydroxyalkyl Ester.

Optionally the combined organic phases are filtered through silica or alumina and/or are stirred with charcoal to achieve improved decolorization. After drying over anhydrous Na2SO4 and filtration the solvent is stripped off in vacuo.

Alternatively an alkylation according to the so-called Carbonate Method according to Houben-Weyl, Methoden der Organischen Chemie, Band VI/3 Teil 3, Sauerstoffverbindungen 1, 4. Auflage, 1965, Georg Thieme Verlag, Stuttgart, p. 55, or a deacylating alkylation of mono or diacylated Dihydroxybenzenes (e.g. RAc or RAc2) according to Houben-Weyl, Methoden der Organischen Chemie, Band VI/3 Teil 3, Sauerstoffverbindungen 1, 4. Auflage, 1965, Georg Thieme Verlag, Stuttgart, p. 59, is possible.

General Procedure B: Synthesis of Diol Precursors (e.g. OER) Via Etherification of Already Alkoxylated Dihydroxybenzenes (e.g. Ethoxylated Resorcinol) with Halogenated Alcohols (e.g. 3-Chloro-1-propanol)

Under a protective gas atmosphere (e.g. nitrogen) to a mixture of the corresponding Already Alkoxylated Dihydroxybenzene and the corresponding Halogenated Alcohol/s a solution of KOtBu in e.g. THF or tBuOH is added slowly at elevated temperature (e.g. 80° C.). After stirring over night at elevated temperature the reaction mixture is cooled to room temperature, the precipitate is separated by filtration, and the solvent is stripped off from the filtrate in vacuo. Optionally further purification of this residue via an aqueous workup as described in General Procedure A can be achieved.

General Procedure C: Synthesis of Ethoxylated Diol Precursors (e.g. ET) Via Etherification of Hydroxyalkylphenols (e.g. Tyrosol) with Ethylene Carbonate To a solution of the corresponding Hydroxyalkylphenol and Ethylene Carbonate in IPA or tBuOH solide alkaline hydroxide (e.g. KOH) or alkaline carbonate (e.g. K2CO3) or alkaline tert-butoxide (e.g. KOtBu) is added and the reaction mixture is stirred at reflux over night. Optionally the synthesis can be done under a protective gas atmosphere (e.g. nitrogen).

The reaction mixture is cooled to room temperature, the solvent is stripped off in vacuo, and then the residue is extracted against water and further worked up as described in General Procedure A. Optionally the isolated product can be further purified by crystallization using water as solvent.

General Procedure D: Synthesis of Diol Precursors (e.g. PGT) Via Addition of Dihydroxybenzenes (e.g. 4-Tert-Butylcatechol) or Hydroxyalkylphenols (e.g. Tyrosol) or Hydroxybenzoic Acids (e.g. mHB) or Already Etherified and/or Nucleophilic Esterified Hydroxybenzoic Acids (e.g. OmHB) onto Epoxies (e.g. GP or GMA) Under Ring-Opening Solvent Base Route: To an aqueous solution of the corresponding Hydroxyalkylphenol (e.g. Tyrosol) and alkaline hydroxide (e.g. NaOH) or alkaline carbonate (e.g. Na2CO3) or ammonia the epoxy (e.g. GP) is added at reflux. Optionally the synthesis can be done under a protective gas atmosphere (e.g. nitrogen). Optionally the synthesis can be done using IPA or HOtBu as solvent and solid alkaline hydroxide (e.g. KOH) or alkaline carbonate (e.g. K2CO3) or alkaline tert-butoxide (e.g. KOtBu). After stirring over night at reflux the reaction mixture is cooled to room temperature, and the reaction mixture is extracted and further worked up as described in General Procedure A.

Solvent Free Route: To the mixture of the corresponding Dihydroxybenzenes (e.g. 4-tert-Butylcatechol) and the epoxy (e.g. GMA) a catalyst (e.g. $PPh_3$ or TEA) is added under stirring and the reaction mixture is warmed to an elevated temperature. Optionally the synthesis can be done under a protective gas atmosphere (e.g. nitrogen). After stirring over night at elevated temperature the reaction mixture is cooled to room temperature, and the reaction mixture is extracted and further worked up as described in General Procedure A.

Optionally the isolated product can be further purified by crystallization using water as solvent or by fractionated subsequent organic-organic extraction using organic solvents of different polarities.

General Procedure E: Acid Catalyzed (e.g. MSA) Esterification of Diol Precursors (e.g. OR) with Unsaturated Acids (e.g. MA)

To the corresponding Diol Precursor in e.g. cyclohexane or a hexane/toluene mixture or a cyclohexane/toluene mixture BHT, HQME, optionally methylene blue and/or HQ, the catalyst (e.g. MSA) and the unsaturated acid (e.g. MA) are added. At reflux water is removed using a Dean Starck apparatus. After completion of the reaction the crude reaction mixture is extracted at least twice with 4N NaOH solution or 2N NaOH solution, then at least once washed with water, and then dried over anhydrous Na2SO4. After filtration, the filtrate is optionally filtered through basic alumina. 100-300 ppm of BHT and 100-300 ppm of HQME are added to the filtrate. Then the solvent is stripped off in vacuo while air is bubbling through the crude sample.

EBP-MA (Comparative Example 1)

commercially available monomer.

OBP-MA (Comparative Example 2)

Synthesis according to DE 19 21 869, Example 11.

ER-MA (Comparative Example 3

According to General Procedure E 118.6 g of ER, 13.0 g of MSA, and 150.3 g of MA were reacted to give 148.2 g of ER-MA as a yellowish oil that crystallizes at room temperature readily to a colorless solid (m.p.>60° C.).

EH-MA (Comparative Example 4)

According to General Procedure E 118.6 g of EH, 13.0 g of MSA, and 150.3 g of MA were reacted to give 118.3 g of EH-MA as a colorless solid (m.p.>80° C.) immediately after synthesis.

E4R-MA (Comparative Example 5)

According to General Procedure A 51.0 g of resorcinol, 47.7 g of NaOH, and 138.5 g of 2-(2-chloroethoxy)-ethanol were reacted in 200 mL of water to give 104.1 g of E4R. According to General Procedure E 190.0 g of E4R, 12.3 g of MSA, and 171.4 g of MA were reacted to give 238.9 g of E4R-MA.

OR-MA (Comparative Example 6)

According to General Procedure A 51.0 g of resorcinol, 48.2 g of NaOH, and 105.1 g of 3-chloro-1-propanol were reacted in 200 mL of water to give 102.7 g of OR. According to General Procedure E 180.0 g of OR, 13.1 g of MSA, and 205.5 g of MA were reacted to give 288.3 g of OR-MA as a yellowish oil that crystallizes at room temperature readily to a colorless solid (m.p.>30° C.).

EER-MA (Inventive Example 1)

According to the subsequent reaction pattern of General Procedure A first 50.0 g of resorcinol, 27.5 g of NaOH, and 55.4 g of 2-chloro-1-ethanol were reacted over night at a reaction temperature of 40° C. in 155 mL of water, then 75.0 g of 2-(2-chloroethoxy)-ethanol and 27.5 g of NaOH dissolved in 44.4 mL of water were added under reflux and the reaction mixture was kept at reflux over night to give 78.2 g of EER. According to General Procedure E 74.0 g of EER, 5.20 g of MSA, and 78.9 g of MA were reacted to give 105.5 g of EER-MA.

OER-MA (Inventive Example 2)

According to General Procedure B 60.0 g of ethoxylated resorcinol (ER), 31.5 g of 3-chloro-1-propanol, and 165.4 g of a 1.7M KOtBu solution in THF were reacted to give 63.5 g of OER. According to General Procedure E 85.0 g of OER, 5.80 g of MSA, and 85.7 g of MA were reacted to give 117.6 g of OER-MA.

OOR-MA (Inventive Example 3)

According to General Procedure B 20.0 g of OR, 8.53 g of 3-chloro-1-propanol, and 88.4 mL of a 1M KOtBu solution in HOtBu were reacted to give 20.3 g of OOR. According to General Procedure E 17.0 g of OOR, 1.10 g of MSA, and 15.4 g of MA were reacted to give 23.2 g of OOR-MA.

OE2R-MA (Inventive Example 4)

According to General Procedure A 51.0 g of resorcinol, 47.7 g of NaOH, 69.2 g of 2-(2-chloroethoxy)-ethanol, and 51.5 g of 3-chloro-1-propanol were reacted in 200 mL of water to give 93.5 g of OE2R. According to General Procedure E 55.0 g of OE2R, 3.80 g of MSA, and 55.4 g of MA were reacted to give 71.4 g of OE2R-MA.

HOR-MA (Inventive Example 5)

According to General Procedure A 51.0 g of resorcinol, 47.7 g of NaOH, 75.9 g of 6-chlorohexanol, and 51.5 g of 3-chloro-1-propanol were reacted in 200 mL of water to give 115.2 g of HOR. According to General Procedure E 70.0 g of HOR, 4.67 g of MSA, and 67.4 g of MA were reacted to give 101.7 g of HOR-MA.

HOR-A (Inventive Example 6)

According to General Procedure E 43.7 g of HOR, 2.68 g of MSA, and 35.2 g of acrylic acid (AA) were reacted to give 54.8 g of HOR-A.

POR-MA (Inventive Example 7)

According to General Procedure A 51.0 g of resorcinol, 47.7 g of NaOH, 68.2 g of 5-chloropentanol, and 51.5 g of 3-chloro-1-propanol were reacted in 200 mL of water to give 85.2 g of POR. According to General Procedure E 81.9 g of POR, 5.60 g of MSA, and 83.2 g of MA were reacted to give 119.8 g of POR-MA.

OE2C-MA (Inventive Example 8)

According to General Procedure A 50.0 g of catechol, 49.0 g of NaOH, 75.0 g of 2-(2-chloroethoxy)-ethanol, and 51.5 g of 3-chloro-1-propanol were reacted in 200 mL of water to give 67.7 g of OE2C. According to General Procedure E 65.0 g of OE2C, 4.40 g of MSA, and 65.5 g of MA were reacted to give 88.3 g of OE2C-MA.

E4RE-MA (Inventive Example 9)

According to General Procedure A 48.8 g of 1,3-dihydroxy-4-ethylbenzene, 64.0 of KOH, and 113.2 g of 2-(2-chloroethoxy)-ethanol were reacted in 280 mL of water to give 58.7 g of E4RE. According to General Procedure E 57.6 g of E4RE, 3.57 g of MSA, and 47.3 g of MA were reacted to give 71.4 g of E4RE-MA.

E4RH-MA (Inventive Example 10)

According to General Procedure A 68.6 g of 1,3-dihydroxy-4-hexylbenzene, 39.2 of NaOH, and 113.2 g of 2-(2-chloroethoxy)-ethanol were reacted in 275 mL of water to give 110.0 g of E4RH. According to General Procedure E 107.0 g of E4RH, 6.20 g of MSA, and 74.6 g of MA were reacted to give 108.2 g of E4RH-MA.

ORE-MA (Inventive Example 11)

According to General Procedure A 49.6 g of 4-ethylresorcinol, 37.7 g of NaOH, and 81.4 g of 3-chloro-1-propanol were reacted in 200 mL of water to give 76.2 g of ORE. According to General Procedure E 72.4 g of ORE, 5.00 g of MSA, and 73.5 g of MA were reacted to give 107.4 g of ORE-MA.

ORH-MA (Inventive Example 12)

According to General Procedure A 32.9 g of 4-hexylresorcinol, 17.8 g of NaOH, and 37.7 g of 3-chloro-1-propanol were reacted in 130 mL of water to give 39.8 g of ORH. According to General Procedure E 39.8 g of ORH, 1.13 g of MSA, and 33.1 g of MA were reacted to give 54.8 g of ORH-MA.

EBC-MA (Inventive Example 13)

According to General Procedure C 30.0 g of 4-tert-butylcatechol, 3.54 g of KOH, and 47.7 g of ethylene carbonate were reacted in 40 g of IPA to give 46.5 g of EBC.

According to General Procedure E 46.0 g of EBC, 2.89 g of MSA, and 38.9 g of MA were reacted to give 65.8 g of EBC-MA.

EEBC-MA (Inventive Example 14)

According to the subsequent reaction pattern of General Procedure A first 37.4 g of 4-tert-butylcatechol, 13.5 g of NaOH, and 27.1 g of 2-chloro-1-ethanol were reacted over night at a reaction temperature of 40° C. in 128 mL of water, then 36.4 g of 2-(2-chloroethoxy)-ethanol and 13.5 g of NaOH dissolved in 22 mL of water were added under reflux and the reaction mixture was kept at reflux over night to give 59.4 g of EEBC. According to General Procedure E 59.4 g of EEBC, 3.77 g of MSA, and 51.4 g of MA were reacted to give 71.8 g of EEBC-MA.

E4BC-MA (Inventive Example 15)

According to General Procedure A 76.2 g of 4-tert-butylcatechol, 47.7 of NaOH, and 138.5 g of 2-(2-chloroethoxy)-ethanol were reacted in 300 mL of water to give 124.9 g of E4BC. According to General Procedure E 58.7 g of E4BC, 3.50 g of MSA, and 44.3 g of MA were reacted to give 45.7 g of E4BC-MA.

OBC-MA (Inventive Example 16)

According to General Procedure A 77.0 g of 4-tertbutylcatechol, 48.2 of NaOH, and 105.1 g of 3-chloro-1-propanol were reacted in 300 mL of water to give 119.1 g of OBC. According to General Procedure E 60.0 g of OBC, 3.91 g of MSA, and 54.9 g of MA were reacted to give 81.0 g of OBC-MA.

OE2BC-MA (Inventive Example 17)

According to General Procedure A 69.6 g of 4-tertbutylcatechol, 45.3 g of NaOH, 67.8 g of 2-(2-chloroethoxy)-ethanol, and 47.1 g of 3-chloro-1-propanol were reacted in 275 mL of water to give 113.2 g of OE2BC. According to General Procedure E 56.7 g of OE2BC, 3.50 g of MSA, and 46.9 g of MA were reacted to give 67.3 g of OE2BC-MA.

BC-GMA (Inventive Example 18)

According to General Procedure D (Solvent Free Route) 50.0 g of 4-tert-butylcatechol, 0.68 g of TEA, and 85.5 g of GMA were reacted at a temperature of 80° C. to give 114.6 g of BC-GMA.

PGT-AM (Inventive Example 19)

According to General Procedure D (Solvent Based Route) 100.0 g of tyrosol, 5.73 g of NaOH, and 108.0 g of GP were reacted in 200 mL of water to give 203.4 g of crude PGT. After re-crystallization from water 188.9 g of purified PGT were collected. According to General Procedure E 218.5 g of purified PGT and 12.5 g of MSA were first reacted with 68.5 g of MA and then reacted with 82.0 g of AA to give 295.2 g of PGT-AM.

ET-MA (Inventive Example 20)

According to General Procedure C 100.0 g of tyrosol, 7.02 g of KOH, and 82.0 g of ethylene carbonate were reacted in 100 g of IPA to give 112.5 g of crude ET. After re-crystallization from water 74.5 g of purified ET were collected. According to General Procedure E 20.0 g of purified ET, 1.48 g of MSA, and 23.6 g of MA were reacted to give 33.2 g of ET-MA.

E2T-MA (Inventive Example 21)

According to General Procedure A 50.0 g of tyrosol, 44.9 og NaOH, and 136.6 g of 2-(2-chloroethoxy)-ethanol were reacted in 200 mL of water to give 88.1 g of E2T. According to General Procedure E 60.0 g of E2T, 2.80 g of MSA, and 22.8 g of MA were reacted to give 85.2 g of E2T-MA.

OT-MA (Inventive Example 22)

According to General Procedure A 40.0 g of tyrosol, 19.7 og KOH, and 34.9 g of 3-chloro-1-propanol were reacted in 40 g of IPA to give 49.7 g of OT. According to General Procedure E 49.70 g of OT, 3.54 g of MSA, and 54.4 g of MA were reacted to give 79.7 g of OT-MA.

MGT-MA (Inventive Example 23)

According to General Procedure D (Solvent Based Route) 51.0 g of tyrosol, 10.9 mL of a 1M KOtBu solution in HOtBu, and 46.8 g of GMA were reacted to give 37.2 g of crude MGT. After fractionated subsequent organic-organic extraction using toluene/hexane mixtures as well as pure cyclohexane and pure hexane to remove unwanted very unpolar as well as unwanted very polar by-products 9.50 g of purified MGT-MA were collected.

Synthesis of Light Curing One Component Compositions

Some of the compounds synthesized were used for producing a (dental) composition.

The compositions produced and tested with respect to their mechanical properties are given in Table 2 below. In Table 2 the values of the components represent %-weight of the individual components in the corresponding dental formulation.

General Procedure I:

With magnetic stirring and under the exclusion of light the initiator system components were dissolved within the monomers at temperatures not above 50° C. (depending on the intrinsic viscosity of the used monomers).

General Procedure II:

According to General Procedure I the initiator system components were dissolved within the monomers. Under the exclusion of light and using a two-arm kneader the filler was mixed in portions with this mixture of initiator system and monomers. The amount of filler was manually determined depending on the desired handling properties of the dental composition. The dental composition was then light cured using a 800 mW halogen curing light (3M ESPE Elipar™ Trilight) and tested according to the corresponding measurements listed above. The respective values are given in Table 2.

Dental Compositions A and B contain either of components CE1 or CE2 but not compound (A) according to the invention. In Table 2 below, compound (A) is represented by components IE1, IE4, and IE20. Thus, Dental Compositions A and B can be considered as Comparative Examples, whereas Dental Compositions C to E can be considered as Inventive Examples.

TABLE 2

| | Dental Composition | | | | |
|---|---|---|---|---|---|
| | A | B | C | D | E |
| CE1 | 22.2 | | | | |
| CE2 | | 22.2 | | | |
| IE1 | | | 22.2 | | |
| IE4 | | | | 22.2 | |
| IE20 | | | | | 22.2 |
| Ini5 | 0.03 | 0.03 | 0.03 | 0.03 | 0.03 |
| Ini6 | 0.19 | 0.19 | 0.19 | 0.19 | 0.19 |
| Ini7 | 0.09 | 0.09 | 0.09 | 0.09 | 0.09 |
| F1 | 7.36 | 7.36 | 7.36 | 7.36 | 7.36 |
| F2 | 70.1 | 70.1 | 70.1 | 70.1 | 70.1 |
| CS 1 [MPa] | 420 ± 21.0 | 387 ± 35.0 | 461 ± 22.0 | 469 ± 21.0 | 445 ± 22.0 |

As can be seen, compositions containing compound (A) according to the invention are superior with respect to compressive strength (CS 1) compared to compositions not containing compound (A) according to the invention.

Synthesis of Chemical Curing Two Component Compositions

Some of the compounds synthesized were used for producing a (dental) composition.

The compositions produced and tested with respect to their mechanical properties are given in Tables 3, 4, 5 and 6.

In Tables 3 and 4 the values of the components represent %-weight of the individual components in the corresponding dental formulation. In Tables 5 and 6 the values of the components Base 1 to CAT represent relative % of the individual components in the corresponding dental formulation.

General Procedure III:

Under the exclusion of light the components listed in Tables 3 and 4 were mixed in a three-arm laboratory kneader. Residual agglomerates were homogenized in a ceramic three-roller mill.

General Procedure IV:

The pastes listed in Tables 3 and 4 that were made according to General Procedure III were filled into the respective compartments of a 10:1 SulzerMixpac™ cartridge. The material was then applied into the respective metal moulds using a Garant™ II 10:1 cartridge equipped with a static mixer (SulzerMixpac Company). Cure was effected under pressure between plastic foil (Hostaphan™ RN75) and plexiglass plates for 1 h at 23° C. Then the press, plexiglass plates, and foil were removed, and the specimens within the moulds were subjected to post-cure at 36° C. under demineralized water for 23 h. The moulds were removed immediately before measurement. The cured specimens were tested according to the corresponding measurements listed above. The respective values are given in Tables 5 and 6.

Dental Composition—Bases 1, 2, and 3 contain either of components CE1, CE2 or CE5 but not compound (A) according to the present invention. In Tables 3 and 4 below, compound (A) is represented by components IE1, 1E2, 1E4, 1E16, 1E19 and 1E20. Thus, Dental Composition—Bases 1, 2, and 3 can be considered as belonging to a Comparative Example, whereas Dental Compositions—Bases 4 to 9 can be considered as belonging to Inventive Examples.

TABLE 3

| | Dental Composition | | | | | |
|---|---|---|---|---|---|---|
| | Base 1 | Base 2 | Base 3 | Base 4 | Base 5 | Base 6 |
| Co1 | 13.1 | 13.1 | 13.1 | 13.1 | 13.1 | 13.1 |
| CE1 | 52.4 | | | | | |
| CE2 | | 52.4 | | | | |
| CE5 | | | 52.4 | | | |
| IE1 | | | | 52.4 | | |
| IE2 | | | | | 52.4 | |
| IE4 | | | | | | 52.4 |
| IE16 | | | | | | |
| IE19 | | | | | | |
| IE20 | | | | | | |
| Ini3 | 0.15 | 0.15 | 0.15 | 0.15 | 0.15 | 0.15 |
| Ini4 | <0.01 | <0.01 | <0.01 | <0.01 | <0.01 | <0.01 |
| F3 | 26.3 | 26.3 | 26.3 | 26.3 | 26.3 | 26.3 |
| F4 | 8.00 | 8.00 | 8.00 | 8.00 | 8.00 | 8.00 |
| Sof1 | | | | | | |
| F4 | | | | | | |
| Ini1 | | | | | | |
| Ini2 | | | | | | |

TABLE 4

| | Dental Composition | | | |
|---|---|---|---|---|
| | Base 7 | Base 8 | Base 9 | CAT |
| Co1 | 13.1 | 13.1 | 13.1 | |
| CE1 | | | | |
| CE2 | | | | |
| CE5 | | | | |
| IE1 | | | | |
| IE2 | | | | |
| IE4 | | | | |
| IE16 | 52.4 | | | |
| IE19 | | 52.4 | | |
| IE20 | | | 52.4 | |
| Ini3 | 0.15 | 0.15 | 0.15 | |
| Ini4 | <0.01 | <0.01 | <0.01 | |
| F3 | 26.3 | 26.3 | 26.3 | |
| F4 | 8.00 | 8.00 | 8.00 | |
| Sof1 | | | | 79.7 |
| F4 | | | | 10.0 |
| Ini1 | | | | 10.0 |
| Ini2 | | | | 0.30 |

Dental Compositions F, G, and H contain Bases 1, 2, or 3 and CAT, compositions which both contain components according to the state of the art. Dental Compositions I to M contain a Base component containing a compound (A) according to the present invention and a CAT component containing components according to the state of the art. Thus, Dental Compositions I to M can be considered as Inventive Examples.

TABLE 5

| | Dental Composition | | | | | |
|---|---|---|---|---|---|---|
| | F | G | H | I | J | K |
| Base 1 | 90.9 | | | | | |
| Base 2 | | 90.9 | | | | |
| Base 3 | | | 90.9 | | | |
| Base 4 | | | | 90.9 | | |
| Base 5 | | | | | 90.9 | |
| Base 6 | | | | | | 90.9 |
| Base 7 | | | | | | |
| Base 8 | | | | | | |
| Base 9 | | | | | | |
| CAT | 9.1 | 9.1 | 9.1 | 9.1 | 9.1 | 9.1 |
| CS 2 [MPa] | 260.0 ± 19.0 | 251.2 ± 13.5 | 235.4 ± 38.0 | 370.5 ± 25.7 | 300.7 ± 34.3 | 325.1 ± 19.1 |

TABLE 6

| | Dental Composition | | |
|---|---|---|---|
| | K | L | M |
| Base 1 | | | |
| Base 2 | | | |
| Base 3 | | | |
| Base 4 | | | |
| Base 5 | | | |
| Base 6 | | | |
| Base 7 | 90.9 | | |
| Base 8 | | 90.9 | |
| Base 9 | | | 90.9 |
| CAT | 9.1 | 9.1 | 9.1 |
| CS 2 [MPa] | 296.0 ± 18.6 | 292.3 ± 14.7 | 285.1 ± 17.2 |

As can be seen, compositions containing compound (A) according to the invention are superior especially with respect to compressive strength (CS 2) compared to compositions not containing compound (A) according to the invention.

The invention claimed is:

1. A dental composition comprising:
Polymerizable monomer (1),
Initiator component(s),
Filler component(s) in an amount of more than 20 wt.-%, wt.-% with respect to the whole weight of the composition,
the polymerizable monomer (1) being characterized by formula (I)

$$\text{(I)}$$

with:
B—O-A-[—O—B'—]$_a$ representing the unsymmetrical monomer backbone as linkage between the reactive (meth)acrylate moieties,
a=0 or 1,
A being selected from:

A being always attached as aryl-alkyl ether onto B and/or B',
B being selected from:
*—(CH$_2$)$_b$—*, *—(CH$_2$—CH$_2$—O—CH$_2$—CH$_2$)—*,
*—(CH$_2$—CH$_2$—O—CH$_2$—CH$_2$—CH$_2$)—*,
*—(CH$_2$—CH$_2$—CH$_2$—O—CH$_2$—CH$_2$—CH$_2$)—*, B being always attached as alkyl ester onto the (meth)acrylate reactive moiety,
b=2 to 6,
B' being selected from *—(CH2)$_{b'}$—*, *—(CH$_2$—CH$_2$—O—CH$_2$—CH$_2$)—*, B' being always attached as alkyl ester onto the (meth)acrylate reactive moiety,
b'=2 to 6,
R=H, methyl,
X being selected from H, methyl, ethyl, hexyl, tert-butyl,
"*" representing those site(s) of a moiety of the monomer, where that moiety is bonded to another moiety of the monomer.

2. The dental composition according to claim 1, the polymerizable monomer (1) being characterized by either formula (Ia) or formula (Ib)

$$\text{(Ia)}$$

with:
B—O-A-O—B' being an unsymmetrical monomer backbone as linkage between the reactive (meth)acrylate moieties, A being selected from

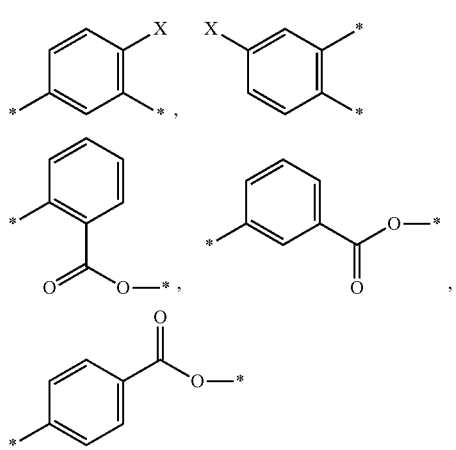

A being always attached as aryl-alkyl ether onto B and B',
B being selected from:

\*—(CH$_2$)$_b$—\*, \*—(CH$_2$—CH$_2$—O—CH$_2$—CH$_2$)—\*,
\*—(CH$_2$—CH$_2$—O—CH$_2$—CH$_2$—CH$_2$)—\*,
\*—(CH$_2$—CH$_2$—CH$_2$—O—CH$_2$—CH$_2$—CH$_2$)—\*,

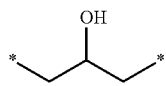

B being always attached as alkyl ester onto the (meth)acrylate reactive moiety,
b=2 to 6,
B' being selected from: \*—(CH$_2$)$_b$—\*, \*—(CH$_2$—CH$_2$—O—CH$_2$—CH$_2$)—\*,

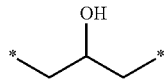 [SMILES: *CC(O)C*]

B' being always attached as alkyl ester onto the (meth)acrylate reactive moiety,
b'=2 to 6,
R=H, methyl,
X=H, methyl, ethyl, hexyl, tert-butyl;
or (Ib)

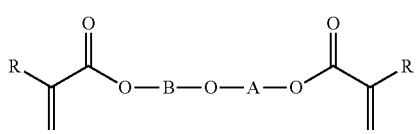

with:
B—O-A being an unsymmetrical monomer backbone as linkage between the reactive (meth)acrylate moieties, A being selected from:

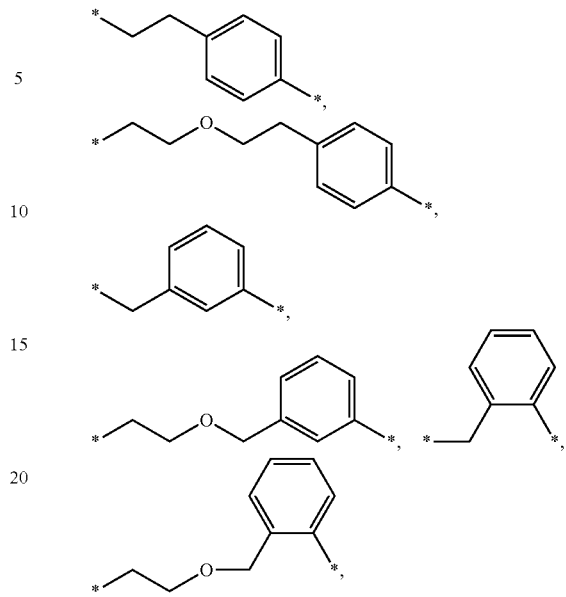

A being always attached as aryl-alkyl ether onto B and always attached as alkyl ester onto the (meth)acrylate reactive moiety,
B being selected from:
\*—(CH$_2$)$_b$—\*, \*—(CH$_2$—CH$_2$—O—CH$_2$—CH$_2$)—\*,

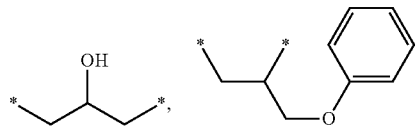

B being always attached as alkyl ester onto the (meth)acrylate reactive moiety,
b=2 to 6,
R=H, methyl;
"\*" representing those sites of a moiety of the monomer, where that moiety is bonded to another moiety of the monomer.

3. The dental composition according to claim 1, wherein the polymerizable monomer (1) has a molecular weight of about 300 to about 600, the polymerizable monomer (1) does not solidify at 23° C. or both.

4. The dental composition according to claim 1, the polymerizable monomer (1) being selected from one of the following monomers and mixtures thereof:

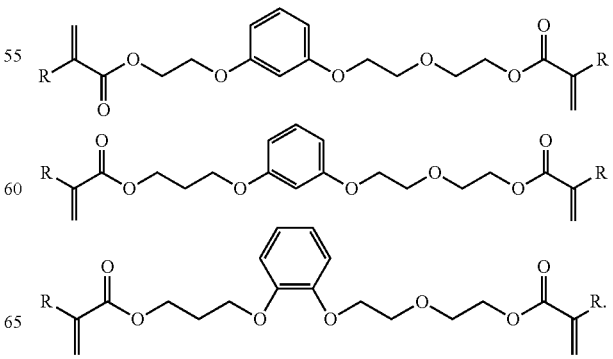

5. The dental composition according to claim 1, the polymerizable monomer (1) being selected from one of the following monomers and mixtures thereof:
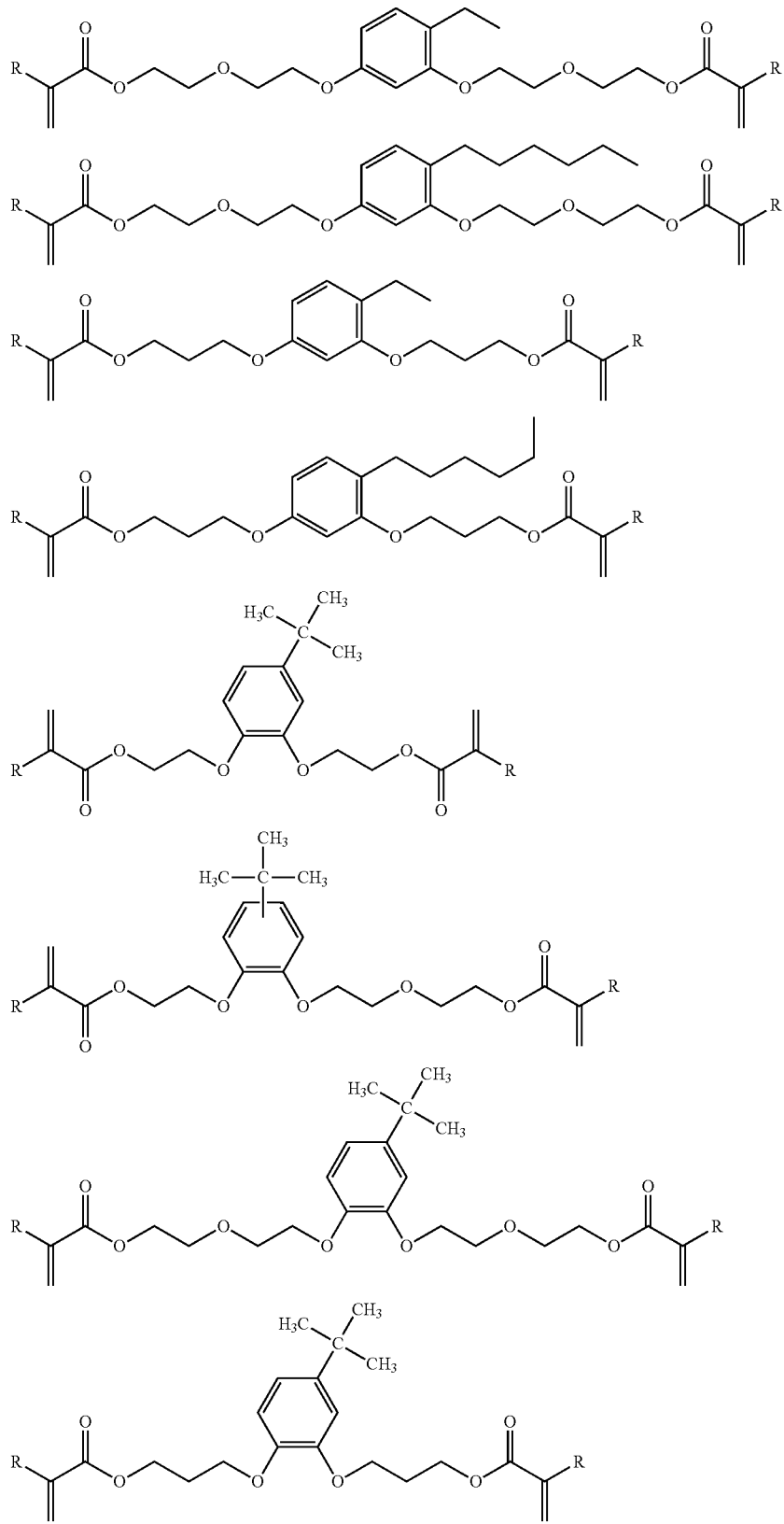

-continued
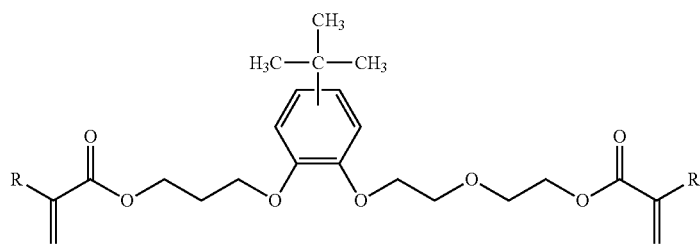
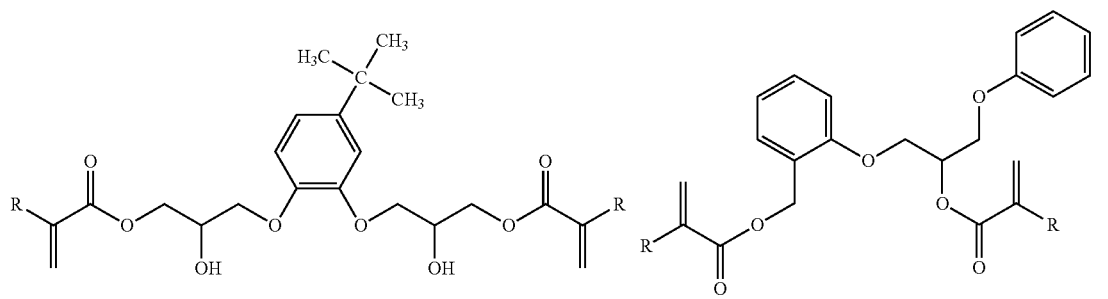
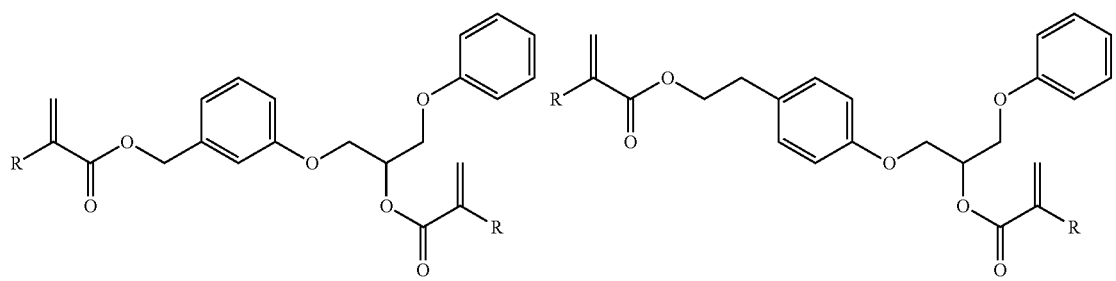
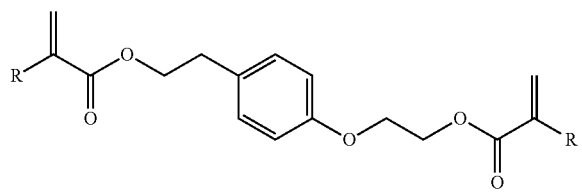
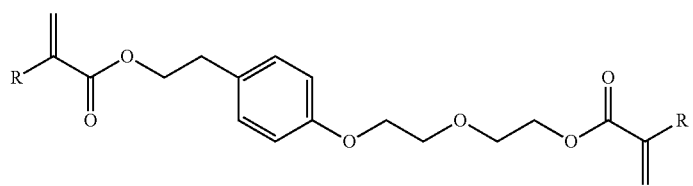
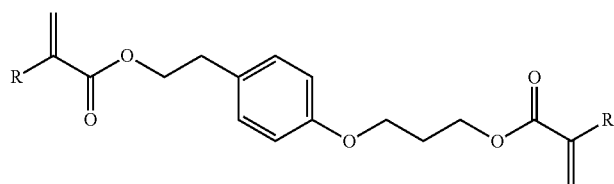
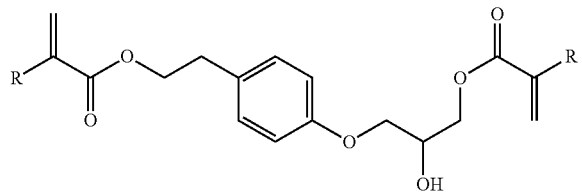

-continued
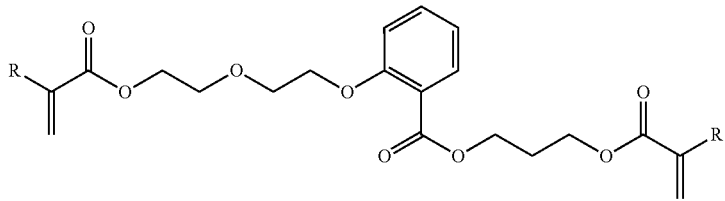
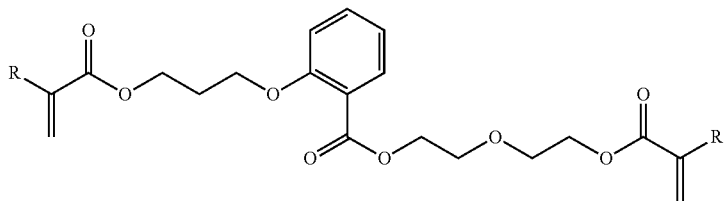
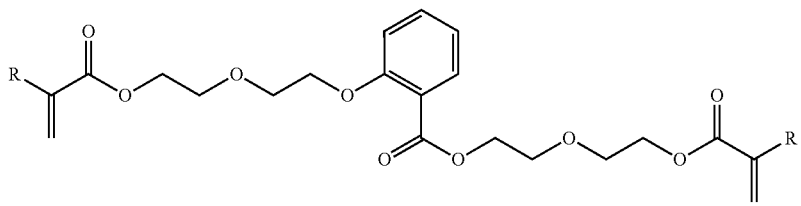
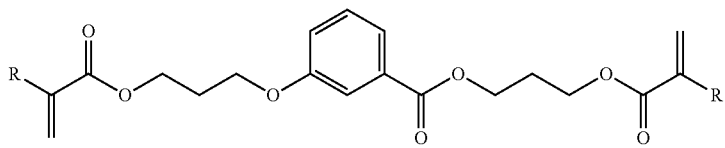
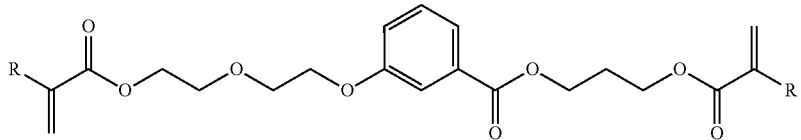
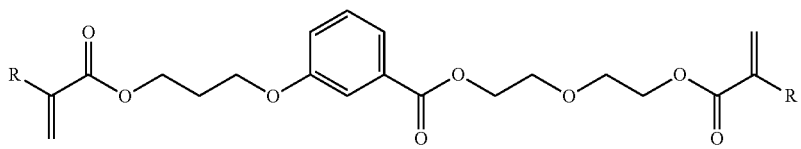
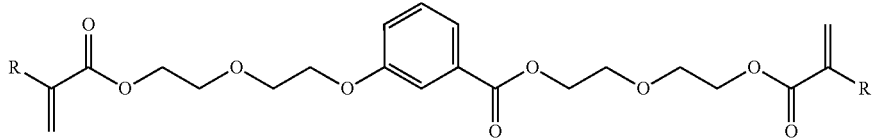
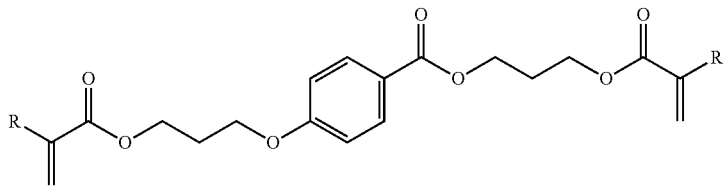
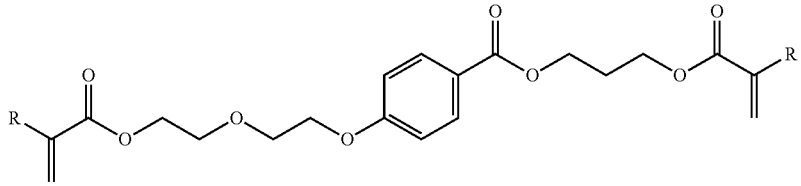

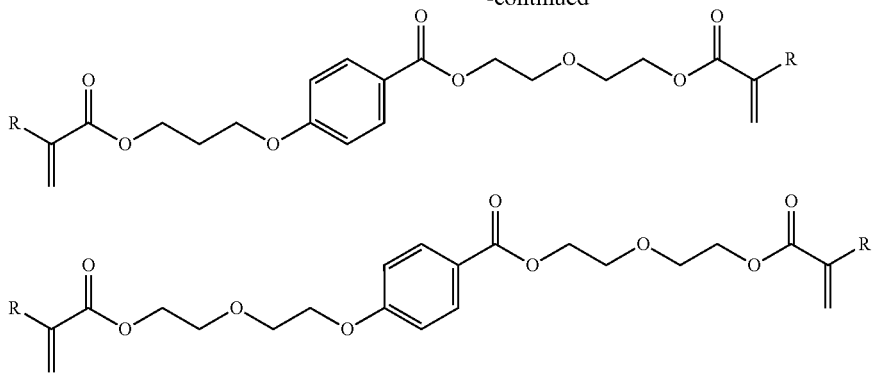

R being always independently selected from H and CH3.

6. The dental composition according to claim 1, the initiator being selected from radiation curing, redox curing, heat curing initiators and combinations thereof.

7. The dental composition according to claim 1 comprising the respective components in the following amounts:
Polymerizable monomer(s) (1): from about 1 to about 75 wt.-%,
Initiator(s): from about 0.1 to about 10 wt.-%,
Filler(s): from about 20 to about 90 wt.-%.

8. The dental composition according to claim 1 further comprising in addition a polymerizable monomer (3) comprising a urethane moiety.

9. The dental composition according to claim 1 not comprising solvent(s) in an amount above about 10 wt.-%.

10. The dental composition according to claim 1, wherein the dental composition has at least one or all of the following features before curing:
Viscosity: from about 0.5 to about 200 Pa*s measured at 23° C. with a shear rate of 100 1/s;
pH value if brought in contact with water: about 1 to about 9,
radiation or redox curing, and
storage stable.

11. The dental composition according to claim 1, wherein the dental composition after curing has a
Compressive strength determined according to ISO 4049 using specimens having the dimension of 3 mm×3 mm×5 mm of at least 430 MPa; and a
Compressive strength determined according to DIN 53454 using cylindrical specimens with a diameter of 4 mm and a height of 8 mm of at least 280 MPa.

12. The dental composition according to claim 1, wherein the
Polymerizable monomer(s) (1) is present in an amount from about 1 to about 75 wt.-%,
Initiator(s), being selected from radiation curing or redox curing initiator(s), and Filler(s) being selected from silica or silica/zirconia filler(s) and mixtures thereof, in an amount from about 20 to about 90 wt.-%.

13. The dental composition according to claim 1 being provided as one or two part system.

14. An article comprising:
the dental composition according to claim 1, the article in the form of a dental filling material, crown and bridge material, inlay, onlay, veneer or dental mill blank.

15. A method comprising:
applying a rapid-prototyping technique to the dental composition according to claim 1 to produce a dental restoration.

16. The method according to claim 15, wherein the dental restoration is selected from a dental crown, a bridge, or an onlay or inlay.

* * * * *

UNITED STATES PATENT AND TRADEMARK OFFICE
CERTIFICATE OF CORRECTION

PATENT NO. : 10,004,669 B2
APPLICATION NO. : 15/119241
DATED : June 26, 2018
INVENTOR(S) : Eckert et al.

Page 1 of 3

It is certified that error appears in the above-identified patent and that said Letters Patent is hereby corrected as shown below:

On the Title Page

Column 1, (Notice)
Line 3, After "0 days." delete "days.".

In the Specification

Column 1
Line 53, After "groups" insert -- . --.

Column 8
Line 38 (approx.), Delete "R=H," and insert -- R=H, --, therefor.

Column 9
Line 40, Delete "R=H," and insert -- R=H, --, therefor.

Column 9
Line 41, Delete "X=H," and insert -- X=H, --, therefor.

Column 10
Line 34 (approx.), Delete "—(CH$_2$)$_b$—*," and insert -- *—(CH$_2$)$_b$—*, --, therefor.

Column 10
Line 46, Delete "R=H," and insert -- R=H, --, therefor.

Column 20
Line 34, Delete "hexandiol" and insert -- hexanediol --, therefor.

Signed and Sealed this
Sixteenth Day of April, 2019

Andrei Iancu
*Director of the United States Patent and Trademark Office*

Column 24
Line 54, Delete "napthylphosphine" and insert -- naphthylphosphine --, therefor.

Column 25
Line 46, Delete "photoinitator" and insert -- photoinitiator --, therefor.

Column 27
Line 21, Delete "photointiators" and insert -- photoinitiators --, therefor.

Column 27
Line 36, Delete "Safranine O," and insert -- Safranin O --, therefor.

Column 28
Line 5, Delete "-dibutyl4-" and insert -- -dibutyl-4- --, therefor.

Column 28
Lines 5-6, Delete "-dimethyl4-" and insert -- -dimethyl-4- --, therefor.

Column 28
Line 6, Delete "-dioctyl4-" and insert -- -dioctyl-4- --, therefor.

Column 28
Line 16, Delete "quarternary" and insert -- quaternary --, therefor.

Column 29
Line 15, Delete "H2O" and insert -- H20 --, therefor.

Column 31
Line 5 (approx.), Delete "Neazopon" and insert -- Neozapon --, therefor.

Column 33
Line 54, Delete "ink jet" and insert -- ink-jet --, therefor.

Columns 37-38
Line 18 (approx.), Delete "HOR-A," and insert -- HOR-A --, therefor.

Columns 53-54
Line 3, Delete "Methylpropenoic" and insert -- Methylpropanoic --, therefor.

Column 55
Line 46 (approx.), Delete "solide" and insert -- solid --, therefor.

Column 56
Line 34 (approx.), Delete "Starck" and insert -- Stark --, therefor.

CERTIFICATE OF CORRECTION (continued)
U.S. Pat. No. 10,004,669 B2

Column 61
Line 63, Delete "1E2, 1E4, 1E16, 1E19 and 1E20." and insert -- IE2, IE4, IE16, IE19 and IE20. --, therefor.

In the Claims

Column 64
Line 47 (approx.), In Claim 1, delete "R=H," and insert -- R=H, --, therefor.

Column 65
Line 39 (approx.), In Claim 2, delete "*—$(CH_2)_b$—*," and insert -- *—$(CH_2)_{b'}$—*, --, therefor.

Column 65
Line 51 (approx.), In Claim 2, delete "R=H," and insert -- R=H, --, therefor.

Column 65
Line 52 (approx.), In Claim 2, delete "X=H," and insert -- X=H, --, therefor.

Column 66
Line 42, In Claim 2, delete "R=H," and insert -- R=H, --, therefor.

Column 65
Line 49, In Claim 3, delete "23° C." and insert -- 23° C., --, therefor.